US008021764B2

(12) United States Patent
Hwang et al.

(10) Patent No.: US 8,021,764 B2
(45) Date of Patent: *Sep. 20, 2011

(54) PHENYLCARBAZOLE-BASED COMPOUND AND ORGANIC ELECTROLUMINESCENT DEVICE EMPLOYING THE SAME

(75) Inventors: Seok-Hwan Hwang, Suwon-si (KR); Young-Kook Kim, Suwon-si (KR); Chang-Ho Lee, Suwon-si (KR); Seok-Jong Lee, Suwon-si (KR); Seung-Gak Yang, Suwon-si (KR); Hee-Yeon Kim, Suwon-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 1134 days.

This patent is subject to a terminal disclaimer.

(21) Appl. No.: 11/286,421

(22) Filed: Nov. 25, 2005

(65) Prior Publication Data

US 2006/0115680 A1    Jun. 1, 2006

(30) Foreign Application Priority Data

Nov. 29, 2004   (KR) .................. 10-2004-0098747

(51) Int. Cl.
*H01L 51/54* (2006.01)
*C07D 209/82* (2006.01)

(52) U.S. Cl. ........ 428/690; 428/917; 313/504; 313/506; 548/440; 548/442; 548/444; 564/427; 564/434; 564/429; 564/428; 564/404; 564/405

(58) Field of Classification Search .................. 313/504, 313/506; 548/440, 442, 444; 564/434, 427, 564/429, 428, 404, 405
See application file for complete search history.

(56) References Cited

U.S. PATENT DOCUMENTS

| 4,356,429 | A | 10/1982 | Tang |
| 6,008,588 | A | 12/1999 | Fujii |
| 6,124,024 | A | 9/2000 | Hosokawa et al. |
| 6,465,115 | B2 | 10/2002 | Shi et al. |
| 6,485,847 | B1 | 11/2002 | Uchida et al. |
| 6,517,957 | B1 | 2/2003 | Senoo et al. |
| 6,596,415 | B2 | 7/2003 | Shi et al. |
| 2001/0010374 | A1 | 8/2001 | Takayama |
| 2003/0076032 | A1* | 4/2003 | Suzuri et al. .................. 313/504 |

(Continued)

FOREIGN PATENT DOCUMENTS

DE    10203328 A1    8/2003

(Continued)

OTHER PUBLICATIONS

Translation of JP 2005-29000, published Oct. 2005.*

(Continued)

*Primary Examiner* — Dawn L Garrett
(74) *Attorney, Agent, or Firm* — Robert E. Bushnell, Esq.

(57) ABSTRACT

A phenylcarbazole-based compound is represented by Formula 1, and has superior electric properties and charge transport abilities, and thus is useful as a hole injection material, a hole transport material, and/or an emitting material which is suitable for fluorescent and phosphorescent devices of all colors, including red, green, blue, and white colors. The phenylcarbazole-based compound is synthesized by reacting carbazole with diamine. The organic electroluminescent device manufactured using the phenylcarbazole-based compound has high efficiency, low voltage, high luminance, and a long lifespan.

15 Claims, 10 Drawing Sheets

U.S. PATENT DOCUMENTS

| | | | |
|---|---|---|---|
| 2003/0224207 | A1 | 12/2003 | Song et al. |
| 2004/0140757 | A1 | 7/2004 | Tyan et al. |
| 2005/0062406 | A1 | 3/2005 | Kinoshita |
| 2005/0067951 | A1 | 3/2005 | Richter et al. |
| 2005/0162074 | A1 | 7/2005 | Madathil et al. |
| 2005/0221124 | A1 | 10/2005 | Hwang et al. |
| 2006/0017377 | A1 | 1/2006 | Ryu |
| 2006/0020136 | A1 | 1/2006 | Hwang et al. |
| 2006/0115680 | A1 | 6/2006 | Hwang et al. |
| 2006/0251924 | A1 | 11/2006 | Lu et al. |
| 2007/0018569 | A1 | 1/2007 | Kawamura et al. |
| 2007/0134512 | A1 | 6/2007 | Klubek et al. |
| 2007/0231503 | A1 | 10/2007 | Hwang et al. |
| 2008/0107919 | A1 | 5/2008 | Hwang et al. |
| 2009/0200928 | A1 | 8/2009 | Hwang et al. |

FOREIGN PATENT DOCUMENTS

| | | | |
|---|---|---|---|
| EP | 1 661 888 A1 | | 5/2006 |
| JP | 62-280850 | | 12/1987 |
| JP | 07-150138 | | 6/1995 |
| JP | 07-234415 | | 9/1995 |
| JP | 08-003547 | | 1/1996 |
| JP | 09-013025 | | 1/1997 |
| JP | 09-268284 | | 10/1997 |
| JP | 10-168443 | | 6/1998 |
| JP | 11-035532 | | 2/1999 |
| JP | 11-144875 | | 5/1999 |
| JP | 11-329734 | | 11/1999 |
| JP | 11-329737 | | 11/1999 |
| JP | 2002-252089 | | 9/2002 |
| JP | 2003-073343 | | 3/2003 |
| JP | 2004-087371 | | 3/2004 |
| JP | 2004-087393 | | 3/2004 |
| JP | 2004-087395 | | 3/2004 |
| JP | 2005-289914 | | 10/2005 |
| JP | 2005-290000 | * | 10/2005 |
| JP | 2005-294504 | | 10/2005 |
| JP | 2006-028176 | | 2/2006 |
| JP | 2006-041471 | | 2/2006 |
| JP | 2006-151979 | | 6/2006 |
| JP | 2007-036188 | | 2/2007 |
| JP | 2007-055996 | | 3/2007 |
| KR | 20050078472 A | | 8/2005 |
| KR | 10-2005-0097670 A | | 10/2005 |
| KR | 2006-0059613 A | | 6/2006 |
| WO | 03-008515 A1 | | 1/2003 |
| WO | WO03/008515 A1 | | 1/2003 |
| WO | 2004/101491 A1 | | 11/2004 |
| WO | 2006/033492 A1 | | 3/2006 |
| WO | 2007/043484 A1 | | 4/2007 |

OTHER PUBLICATIONS

Translation of JP 2004-087395, published Mar. 2004.*
Translation of JP 2004-087393, published Mar. 2004.*
*Office action* from the Korean Intellectual Property Office issued in Applicant's corresponding Korean Patent Application No. 10-2004-0098747 dated Dec. 21, 2006.
European Office Action of the European Patent Application No. 05 11 1348, mailed on Mar. 10, 2006.
An article "Light-Emitting Carbazole Derivatives: Potential Electroluminescent Materials" written by Thomas, et al., published in Journal of the American Chemical Society , 123(38), pp. 9404-9411 in 2001.
Transmitter letter Japanese Office Action issued by Japanese Patent Office on Jun. 16, 2009 in the corresponidng Japanese Patent Application No. 2005-342448.
K.R. Justin Thomas et al., "Light-Emitting Carbazole Derivatives: Potential Electroluminscent Materials", Journal of the American Chemical Society, 2001, vol. 123, No. 38, pp. 9404-9411.
Office action from the State intellectual Property Office, P.R. China issued in Applicant's corresponding Chinese Patent Application No. 200510121732.7 dated Jun. 26, 2009.
Korean Registration Determination Certificate issued by Korean Patent Office on Nov. 29, 2007, corresponding to Korean Patent Application No. 2004-0098747 and Request for Entry of the Accompanying Documents attached herewith.
Shen, et al., "High Tg Blue emitting material for electroluminescent devices", Journal of Materials Chemistry, Issue 15, pp. 2455-2463, May 12, 2005 which was cited in the Office (Paper No. 20080107) mailed Jan. 15, 2008 of the related U.S. Appl. No. 11/097,182.
Thomas, et al., "Green and Yellow Electroluminescent Dipolar Carbazole Derivatives: Features and Benefits of Electron-Withdrawing Segments", American Chemical Society, Issue 14, pp. 3852-3589, Aug. 8, 2008 which was cited in the Information Disclosure Statement filed on Oct. 29, 2008 of the related of the related U.S. Appl. No. 11/097,182.
Adachi, et al., "Endothermic energy transfer: A mechanism for generating very efficient high-energy phosphorescent emission in organic materials", Applied Physics Letters, vol. 79, No. 14, pp. 2082-2084, Sep. 24, 2001, which was cited in the Information Disclosure Statement filed on Mar. 24, 2009 of the related of the related U.S. Appl. No. 12/097,182.
Chinese Office Action issued by Chinese Patent Office on Dec. 26, 2008, with English translation attached, which was cited in the Information Disclosure Statement filed on Feb. 4, 2009 of the related of the related U.S. Appl. No. 11/097,182.
Kuwabara, et al., "Thermally Stable Multilayered Organic Electroluminescent Devices Using Novel Starburst Molecules, 4, 4', 4"-Tri(N-carbazolyl)triphenylamine (TCTA) and 4, 4', 4"-Tris(3-methylphenylphenylamino) triphenylamino (m-MTDATA), as Hole-Transport Materials", Advanced Materials, (1994), vol. 6, No. 9, pp. 677-679, which was cited in the Information Disclosure Statement filed on May 16, 2008 of the related of the related U.S. Appl. No. 12/122,143.
Korean Office Action issued by Korean Patent Office on Oct. 27, 2009, in Application No. 10-2008-0012206, which was cited in the Information Disclosure Statement filed on Jan. 20, 2009 of the related U.S. Appl. No. 12/336,459.
Korean Registration Certificate issued by Korean Patent Office on May 31, 2010, in Application No. 10-2008-0012206, which was cited in the Information Disclosure Statement filed on Jun. 25, 2010 of the related U.S. Appl. No. 12/336,459.
Japanese Office Action issued by Japanese Patent Office on Jun. 1, 2010, in Application No. 2007-110746, which was cited in the Information Disclosure Statement filed on Jun. 28, 2010 of the related U.S. Appl. No. 11/806,039.
European Office Action issued by European Patent Office on Nov. 7, 2007, in Application No. 07109066.6, which was cited in the Information Disclosure Statement filed on Dec. 3, 2007 of the related of the related U.S. Appl. No. 11/806,039.
European Office Action issued by European Patent Office on Jul. 24, 2007, in Application No. 07109066.6, which was cited in the Information Disclosure Statement filed on Dec. 3, 2007 of the related U.S. Appl. No. 11/806,039.
Office Action (Paper No. 20101118) mailed Nov. 24, 2010 of U.S. Appl. No. 12/336,459.
Office Action (Paper No. 20080627) mailed Jul. 8, 2008 of U.S. Appl. No. 11/097,182.
Office Action (Paper No. 20080107) mailed Jan. 15, 2008 of U.S. Appl. No. 11/097,182.
Office Action (Paper No. 20110325) mailed Apr. 1, 2011 of U.S. Appl. No. 12/122,143.
Office Action (Paper No. 20100121) mailed Feb. 8, 2010 of U.S. Appl. No. 11/806,039.
Office Action (Paper No. 20110502) mailed May 10, 2011 of U.S. Appl. No. 11/806,039.
Thomas, et al., "Light-Emitting Carbazole Derivatives: Potential Electroluminescent Materials", Journal of the American Chemical Society, 2001, vol. 123, No. 38 p. 9404-9411, which was cited in the Office Action (Paper No. 20080107) mailed Jan. 15, 2008 of the related U.S. Appl. No. 11/097,182.

* cited by examiner

PHENYLCARBAZOLE-BASED COMPOUND AND ORGANIC ELECTROLUMINESCENT DEVICE EMPLOYING THE SAME

CROSS-REFERENCE TO RELATED PATENT APPLICATION AND CLAIM OF PRIORITY

This application claims the benefit of Korean Patent Application No. 10-2004-0098747, filed on Nov. 29, 2004, in the Korean Intellectual Property Office, the disclosure of which is incorporated herein in its entirety by reference.

BACKGROUND OF THE INVENTION

1. Field of the Invention

The present invention relates to a phenylcarbazole-based compound and an organic electroluminescent device employing the same, and more particularly, to a phenylcarbazole-based compound which has electric stability, superior charge transport ability and high glass transition temperature and can prevent crystallization, and an organic electroluminescent device using an organic layer including the same.

2. Description of the Related Art

An electroluminescent (EL) device is a self-emission type display device and has received significant attention owing to its merits of a wide viewing angle, superior contrast, and rapid response. EL devices are divided into inorganic EL devices in which an emitting layer is composed of an inorganic compound, and organic EL devices in which an emitting layer is composed of an organic compound. An organic EL device has superior luminance, driving voltage, and response rate to an inorganic EL device and can display multicolors, and thus much research into organic EL devices has been conducted.

The organic EL device generally has a layered structure of anode/organic emitting layer/cathode. When a hole transport layer and/or a electron injection layer is further interposed between the anode and the emitting layer or between the emitting layer and the cathode, an anode/hole transport layer/organic emitting layer/cathode structure or an anode/hole transport layer/organic emitting layer/electron injection layer/cathode structure is formed.

The hole transport layer is known to be composed of polyphenyl hydrocarbon or an anthracene derivative (see, for example, U.S. Pat. Nos. 6,596,415 and 6,465,115).

Organic EL devices including hole transport layers composed of conventional materials are not satisfactory in terms of lifespan, efficiency and power consumption, and thus a material for a hole transport layer with a significant improvement in such characteristics is required.

SUMMARY OF THE INVENTION

The present invention provides an organic layer material which has electric stability, superior charge transport ability, and high glass transition temperature, can prevent crystallization, and is suitable for fluorescent and phosphorescent devices having all colors, including red, green, blue, and white colors, etc., and a method of preparing the same.

The present invention also provides an organic EL device using an organic layer composed of the above-described material and having high efficiency, low voltage, high luminance and long lifespan.

According to an aspect of the present invention, there is provided a phenylcarbazole-based compound represented by Formula (1):

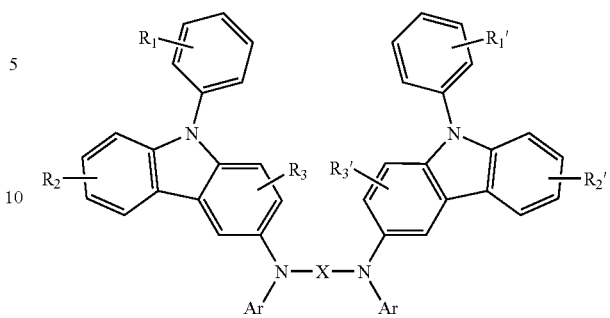

where X is a substituted or unsubstituted C1-C30 alkylene group, a substituted or unsubstituted C2-C30 alkenylene group, a substituted or unsubstituted C6-C30 arylene group, a substituted or unsubstituted C2-C30 heteroarylene group, or a substituted or unsubstituted C2-C30 heterocycle; each of $R_1$, $R_2$, $R_3$, $R_1'$, $R_2'$ and $R_3'$ is independently mono-substituted or multi-substituted substituent and a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C2-C30 heterocycle, a substituted or unsubstituted C6-C30 condensed polycyclic group, a hydroxy group, a cyano group, or a substituted or unsubstituted amino group, and two or more adjacent groups among $R_1$, $R_2$, $R_3$, $R_1'$, $R_2'$ and $R_3'$ can be connected to each other to form a saturated or unsaturated carbocycle; and each Ar is a substituted or unsubstituted C6-C30 aryl group or a substituted or unsubstituted C2-C30 heteroaryl group.

According to another aspect of the present invention, there is provided an organic EL device including a first electrode, a second electrode, and an organic layer interposed therebetween, in which the organic layer contains the phenylcarbazole-based compound.

The organic layer may be a hole injection layer, a hole transport layer, or a single layer serving as both the hole injection layer and the hole transport layer.

In an embodiment of the present invention, the organic layer is a hole injection layer or a hole transport layer, and the organic EL device has a first electrode/hole injection layer/emitting layer/second electrode structure, a first electrode/hole injection layer/emitting layer/hole transport layer/second electrode structure, or a first electrode/emitting layer/hole transport layer/second electrode structure.

The organic layer is an emitting layer, in which the emitting layer is composed of a phosphorescent or fluorescent material.

In the emitting layer, the phenylcarbazole-based compound represented by Formula (1) is used as a fluorescent or phosphorescent host.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
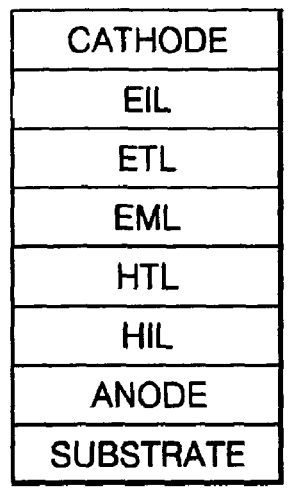
FIG. 1 is a cross-sectional view of an organic electroluminescent device according to an embodiment of the present invention.

Hereinafter, the present invention will be described in more detail.

The present invention provides a phenycarbazole-based compound having at least two phenylcarbazole derivatives as side chains in a molecule, a method of preparing the same, and an organic EL device using the compound as a material for an organic layer such as a hole injection layer, a hole transport layer, or an emitting layer.

The phenylcarbazole-based compound may be preferably represented by Formula 1:

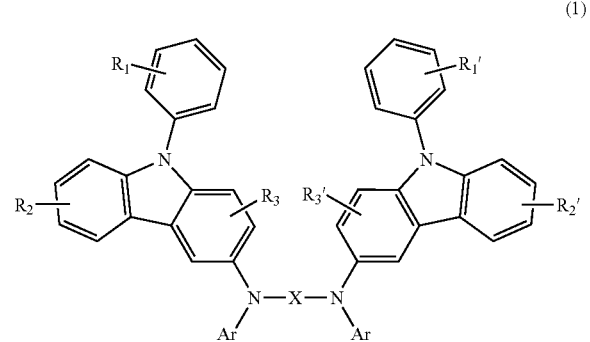

(1)

where X is a substituted or unsubstituted C1-C30 alkylene group, a substituted or unsubstituted C2-C30 alkenylene group, a substituted or unsubstituted C6-C30 arylene group, a substituted or unsubstituted C2-C30 heteroarylene group, or a substituted or unsubstituted C2-C30 heterocycle; each of $R_1$, $R_2$, $R_3$, $R_1'$, $R_2'$ and $R_3'$ is independently mono-substituted or multi-substituted substituent and a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C2-C30 heterocycle, a substituted or unsubstituted C6-C30 condensed polycyclic group, a hydroxy group, a cyano group, or a substituted or unsubstituted amino group, and two or more adjacent groups among $R_1$, $R_2$, $R_3$, $R_1'$, $R_2'$ and $R_3'$ can be connected to each other to form a saturated or unsaturated carbocycle; and each Ar is a substituted or unsubstituted C6-C30 aryl group or a substituted or unsubstituted C2-C30 heteroaryl group.

Each Ar may be a phenyl group, an ethylphenyl group, an ethylbiphenyl group, an o-, m-, or p-fluorophenyl group, a dichlorophenyl group, a dicyanophenyl group, a trifluoromethoxyphenyl group, an o-, m-, or p-tolyl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentarenyl group, an indenyl group, a naphthyl group, a methylnaphthyl group, an anthracenyl group, an azurenyl group, a heptarenyl group, an acenaphthylrenyl group, a phenanthrenyl group, a fluorenyl group, an anthraquinolyl group, a triphenylene group, a pyrenyl group, a pherylenyl group, a chloropherylenyl group, a pentaphenyl group, a pentacenyl group, a tetraphenylenyl group, a hexaphenyl group, a coroneryl group, a trinaphthylenyl group, a heptaphenyl group, or a carbazolyl group.

Preferably, Ar may be a phenyl group, a lower alkylphenyl group, a lower alkoxyphenyl group, a cyanophenyl group, a phenoxyphenyl group, a halophenyl group, a naphthyl group, a lower alkylnaphthyl group, a lower alkoxynaphthyl group, a cyanonaphthyl group, a halonaphthyl group, a fluorenyl group, a carbazolyl group, a lower alkylcarbazolyl group, a biphenyl group, a lower alkylbiphenyl group, a lower alkoxybiphenyl group, a thiophenyl group, an indolyl group, or a pyridyl group. The lower alkyl and lower alkoxy may have 1-5 carbon atoms. More preferably, Ar is a monocyclic, bicyclic, or tricyclic aryl group selected from a fluorenyl group, a carbazolyl group, a phenyl group, a naphthyl group, and a phenanthrenyl group, or an aryl group substituted with one to three, preferably one C1-C3 lower alkyl, C1-C3 lower alkoxy, cyano, phenoxy, phenyl, or halogen on an aromatic ring thereof.

In Formula (1), one or more atoms of Ar may be substituted with a C1-C10 alkyl group, a C1-C10 alkoxy group, a nitro group, a halogen atom, an amino group, a C6-C10 aryl group, a C2-C10 heteroaryl group, a cyano group, a hydroxy group, etc.

The phenycarbazole-based compound represented by Formula (1) has a high glass transition point or melting point due to a rigid carbazole group in its structure. Thus, the organic layer composed of the phenycarbazole-based compound represented by Formula (1) has an increased resistance to joule heat generated in organic layers, between such organic layers, or between such an organic layer and a metal electrode when electroluminescence occurs, and an increased resistance to high temperature conditions, compared with the conventional organic layer. Therefore, when the compound represented by Formula (1) is used as a host material of a hole injection layer, a hole transport layer, or an emitting layer, it exhibits high luminance and can emit light for a long time. In particular, since this compound has at least two rigid carbazole groups in its molecule, the effects are further increased.

The compound represented by Formula (1) may be preferably a compound represented by Formula (2):

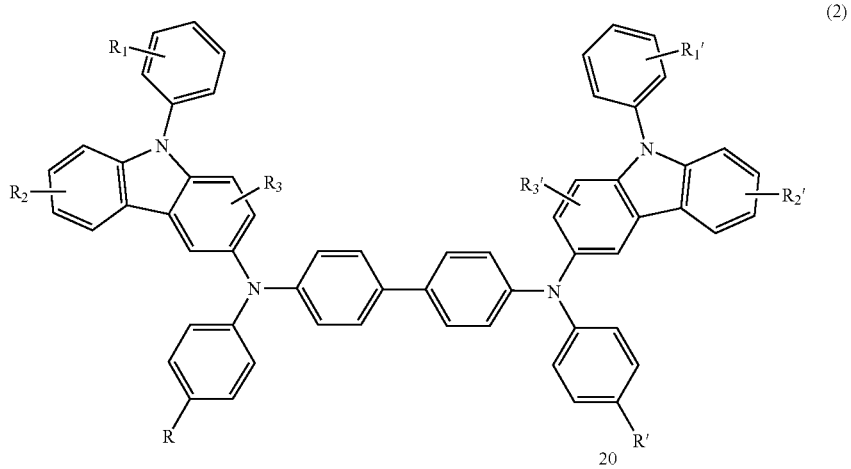

(2)

where each of $R_1$ to $R_3$ and $R_1'$ to $R_3'$ is independently a hydrogen atom, a fluorine atom, a cyano group, a substituted or unsubstituted C1-C30 alkyl group, a substituted or unsubstituted C6-C30 aryl group, a substituted or unsubstituted C2-C30 heterocycle, or a substituted or unsubstituted amino group; and each of R and R' is a hydrogen atom, a cyano group, a fluorine atom, a substituted or unsubstituted C1-C30 alkyl group, a substituted or unsubstituted C6-C30 aryl group, a substituted or unsubstituted C2-C30 heterocycle, or a substituted or unsubstituted amino group.

An organic EL device of the present invention has high durability when it is stored and operated. This is because the phenylcarbazole derivative has a high glass transition temperature Tg. The compound represented by Formula (1) serves as a hole injection material, a hole transport material, and/or an emitting material. Representative structures of novel compounds of the present invention are represented by Formulae 3 through 26, but are not limited thereto:

3

4

-continued

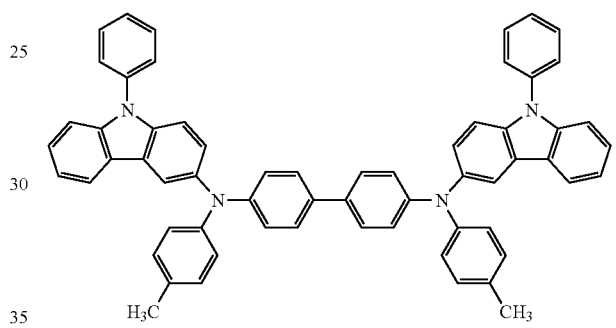

5

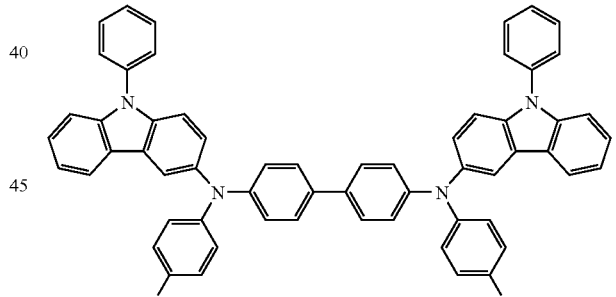

6

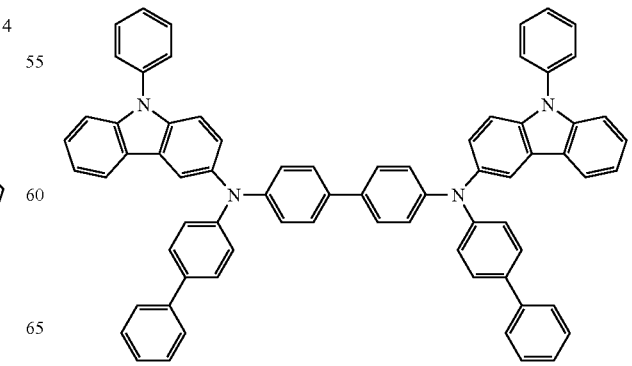

7

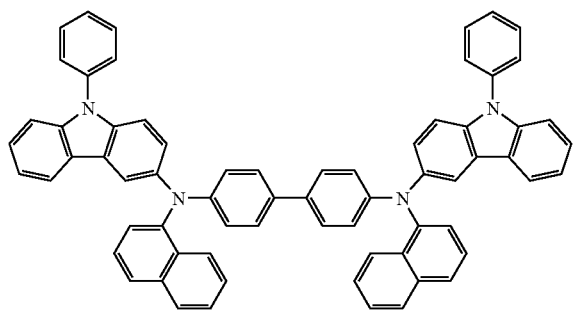
8
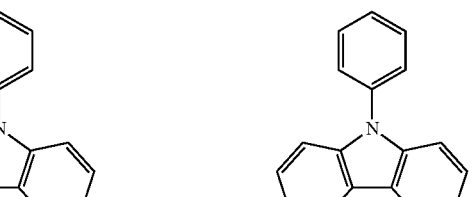
12
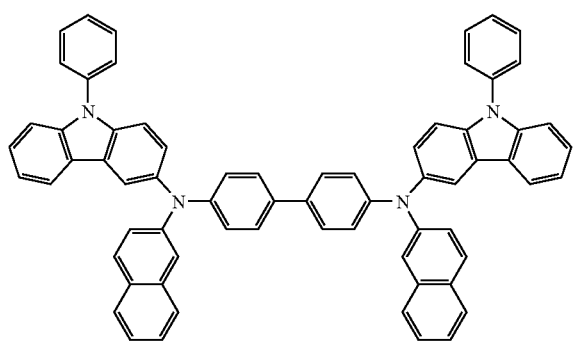
9
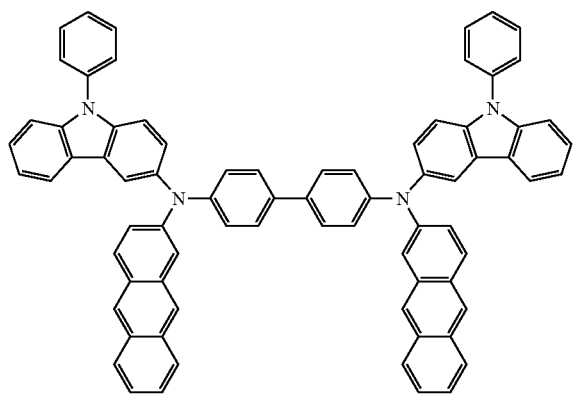
10
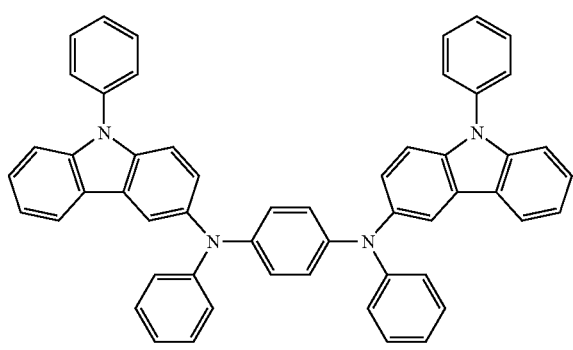
11
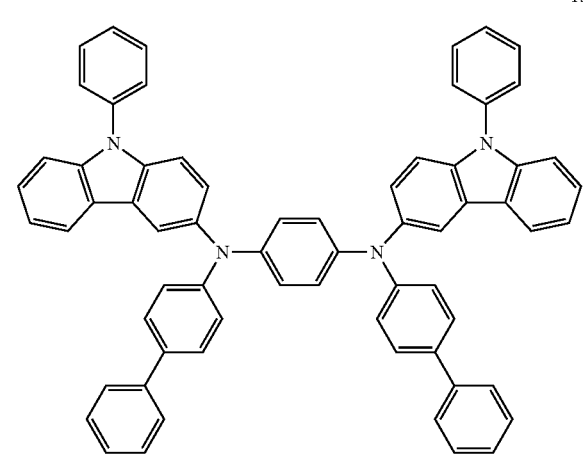

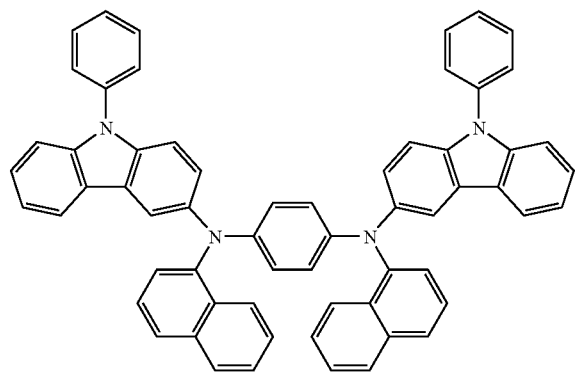
16
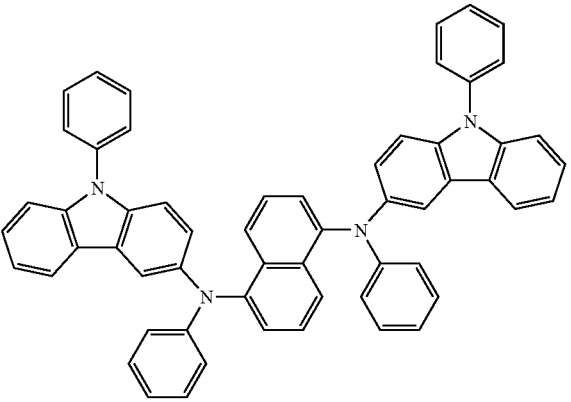
19
17
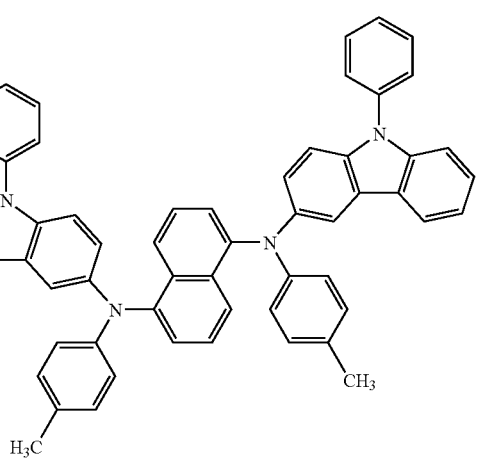
20
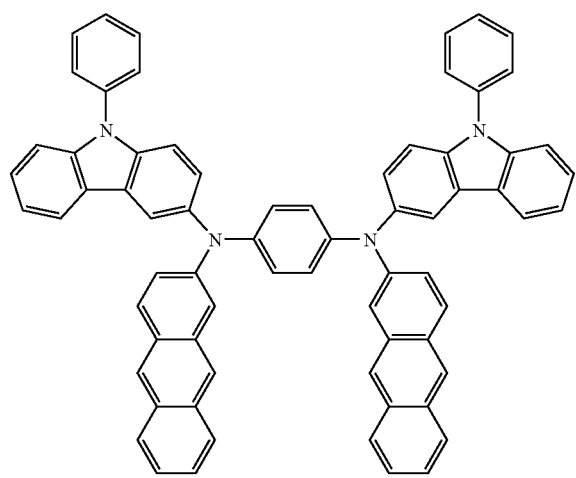
18
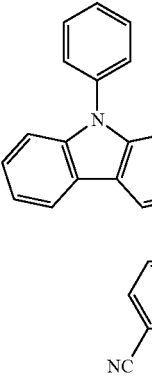
21

22
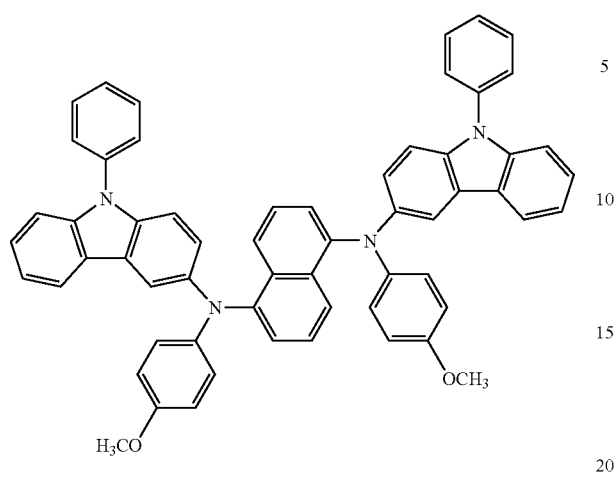
25
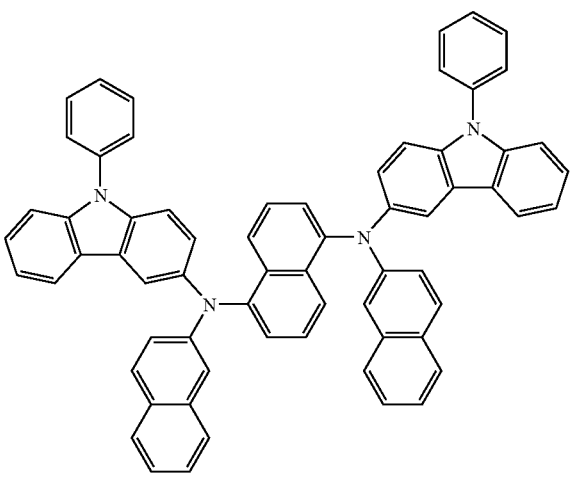
23
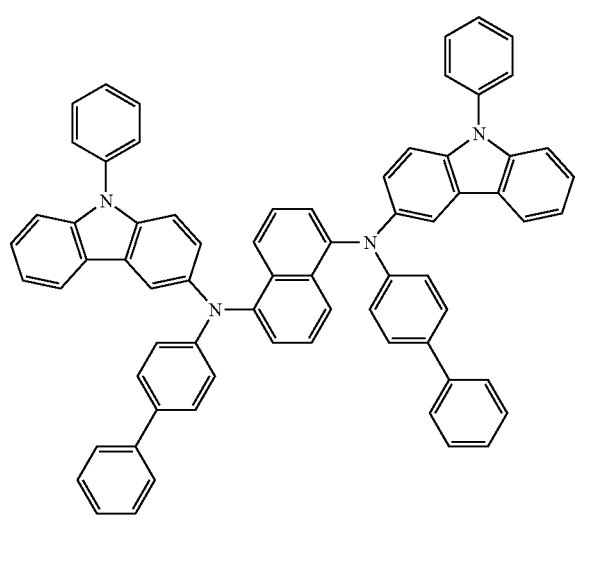
26
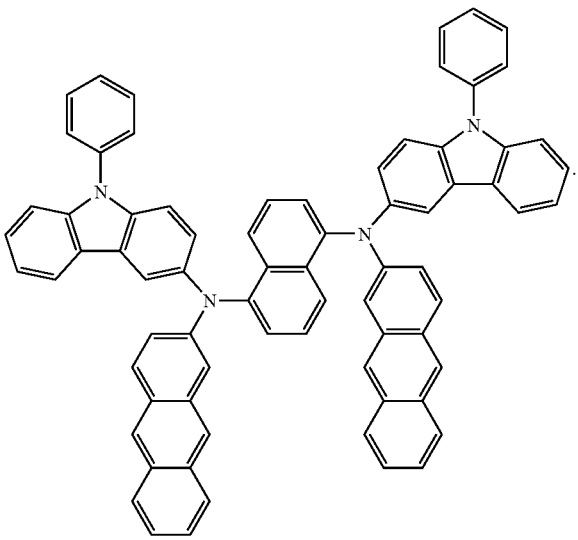
24
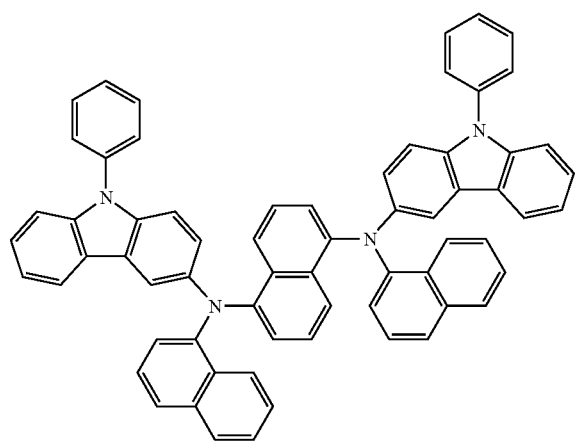
A method of preparing the phenylcarbazole-based compound represented by Formula (1) will now be described.
As set forth in the reaction scheme 1, the phenylcarbazole-based compound represented by Formula (1) is obtained by reacting carbazole (B') with a diamine compound (C').
Reaction Scheme 1
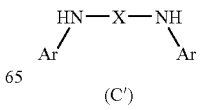
(C')

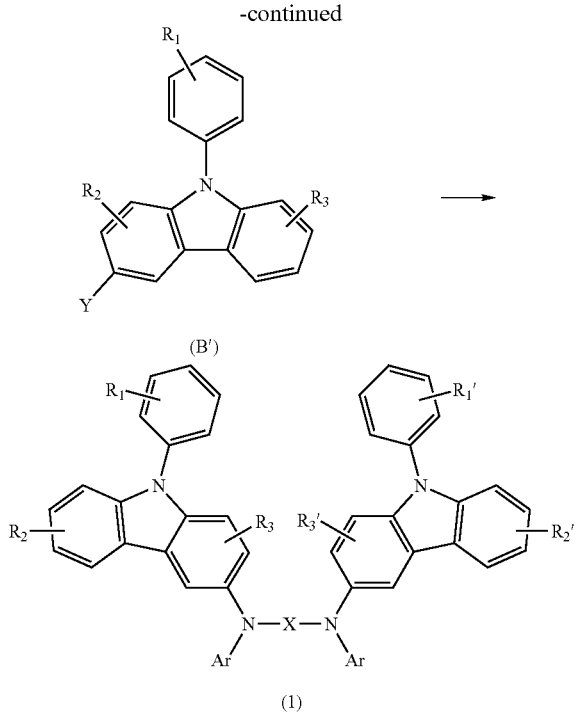

In above Reaction Scheme 1, X is a substituted or unsubstituted C1-C30 alkylene group, a substituted or unsubstituted C2-C30 alkenylene group, a substituted or unsubstituted C6-C30 arylene group, a substituted or unsubstituted C2-C30 heteroarylene group, or a substituted or unsubstituted C2-C30 heterocycle; each of $R_1$, $R_2$, $R_3$, $R_1'$, $R_2'$ and $R_3'$ is independently mono-substituted or multi-substituted substituent and a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C2-C30 heterocycle, a substituted or unsubstituted C6-C30 condensed polycyclic group, a hydroxy group, a cyano group, or a substituted or unsubstituted amino group, and two or more adjacent groups among $R_1$, $R_2$, $R_3$, $R_1'$, $R_2'$ and $R_3'$ can be connected to each other to form a saturated or unsaturated carbocycle; each Ar is a substituted or unsubstituted C6-C30 aryl group or a substituted or unsubstituted C2-C30 heteroaryl group; and Y is a halogen atom.

The reaction is carried out in the presence of $Pd_2(dba)_3$ (dba=dibenzylideneacetone), sodium tert-butoxide, and tri(tert-butyl)phosphine at a temperature of 50 to 150° C.

In the organic EL device of the present invention, an organic layer containing the phenylcarbazole-based compound represented by Formula (1) may be a hole injection layer or a hole transport layer, or a single layer serving as both a hole injection layer and a hole transport layer. An organic layer containing the phenylcarbazole-based compound represented by Formula (1) may be an emitting layer.

When the organic layer containing the phenylcarbazole-based compound represented by Formula (1) is a hole injection layer or a hole transport layer, the device has a first electrode/hole injection layer/emitting layer/second electrode structure, a first electrode/hole injection layer/emitting layer/hole transport layer/second electrode structure, or a first electrode/emitting layer/hole transport layer/second electrode structure, but not limited thereto.

The emitting layer is composed of a phosphorescent or fluorescent material.

When the organic layer containing the phenylcarbazole-based compound represented by Formula (1) is the emitting layer, the phenylcarbazole-based compound is used as a fluorescent or phosphorescent host.

A method of manufacturing an organic electroluminescent device according to an embodiment of the present invention will now be described.

FIG. 1 is a cross-sectional view of an organic electroluminescent device according to an embodiment of the present invention.

First, a material for forming an anode, which has a high work function, is deposited or sputtered on a substrate to form an anode. Any substrate used in a conventional organic EL device can be used, and a glass substrate or a transparent plastic substrate having good mechanical strength, thermal stability, transparency, surface softness, manageability, and water-proofness may be preferably used. The anode may be composed of indium tin oxide (ITO), indium zinc oxide (IZO), tin oxide ($SnO_2$), or zinc oxide (ZnO), which is transparent and have good conductivity.

Next, a hole injection layer (HIL) is formed on the anode using a vacuum evaporation, spin coating, casting, or Langmuir-Blodgett (LB) method. The HIL may be formed using the vacuum evaporation method, since it is easy to obtain uniform film quality and the generation of pinholes is suppressed.

When the HIL is formed using the vacuum evaporation method, the deposition conditions can be varied according to the type of compound used as a hole injection material, and the desired structure and thermal property of the HIL, but may include a deposition temperature of 50 to 500° C., a vacuum of $10^{-8}$ to $10^{-3}$ torr, a deposition rate of 0.01 to 100 Å/sec, and a film thickness of 10 Å to 5 μm.

A HIL material is not particularly restricted, but may be the compound represented by Formula (1), a phthalocyanine-based compound, such as CuPc, as disclosed in U.S. Pat. No. 4,356,429 which is incorporated herein by reference, or a Starburst type amine derivatives, for example, TCTA, m-MTDATA, or m-MTDAPB, as described in Advanced Material, 6, p. 677 (1994) which is incorporated herein by reference.

Then, a hole transport layer (HTL) is formed on the HIL using a vacuum evaporation, spin coating, casting, or Langmuir-Blodgett method. The HTL may be formed using the vacuum evaporation method, since it is easy to obtain uniform film quality and the generation of pinholes is suppressed. When the HTL is formed using the vacuum evaporation method, the deposition conditions vary according to the type of compound to be used, but may be almost identical to the deposition conditions for the HIL.

A HTL material is not particularly restricted, but may be the phenylcarbazole-based compound represented by Formula (1), or any compound known to be used in the HTL. For example, carbazole derivatives, such as N-phenylcarbazole and polyvinylcarbazole, general amine derivatives having an aromatic condensed ring, such as N,N'-bis(3-methylphenyl)-N,N'-diphenyl-[1,1-biphenyl]-4,4'-diamine (TPD), N,N'-di(naphthalen-1-yl)-N,N'-diphenyl benzidine (α-NPD), etc. are used.

Then, an emitting layer (EML) is formed on the HTL using a vacuum evaporation, spin coating, casting, or Langmuir-Blodgett method. The EML may be formed using the vacuum evaporation method since it is easy to obtain uniform film quality and the generation of pinholes is suppressed. When the EML is formed using the vacuum evaporation method, the deposition conditions vary according to the type of compound to be used, but may be almost identical to the deposition conditions for the HIL.

An EML material is not particularly restricted, but may be the phenylcarbazole-based compound represented by Formula (1) as a fluorescent or phosphorescent host. Alq$_3$ (tris (8-quinolinolate) aluminum) may be used as a fluorescent host. IDE102 and IDE105 available from Idemitsu Kosan Co., Ltd., and C545T available from Hayashibara may be used as fluorescent dopants, and Ir(PPy)$_3$ (PPy=phenylpyridine) (green), F2Irpic (bis[2-(4,6-difluorophenyl)pyridinato-N,C2'] iridium picolinate) (blue), and RD61 (red) may be vacuum evaporated (doped) in combination as phosphorescent dopants.

The concentration of the dopant is not particularly restricted, but is typically 0.01-15 parts by weight based of total 100 parts by weight of the host and the dopant.

When the phosphorescent dopant is used in the EML, a hole blocking material is vacuum evaporated or spin coated on the EML to form a hole blocking layer (HBL), in order to prevent a triplet exciton or a hole from diffusing into the ETL. The hole blocking material is not particularly restricted, but may be selected from materials which are used as a hole blocking material in the art. For example, oxadiazole derivatives or triazole derivatives, phenanthroline derivatives, or hole blocking materials described in JP 11-329734 (A1) which is incorporated herein by reference and the like may be used and, more particularly, bis(2-methyl-8-quinolinolato)(4-phenylphenolato)aluminum (BAlq), 2,9-dimethyl-4,7-diphenyl-1,10-phenanthroline (BCP) are used.

Then, an electron transport layer (ETL) is formed using a vacuum evaporating, spin coating, or casting method. Preferably, the ETL is formed using the vacuum evaporating method. An ETL material may be any material which can stably transport electrons injected from an electron injection electrode (cathode) and, more particularly, tris(8-quinolinolate) aluminum (Alq$_3$) may be used. In addition, an electron injection layer (EIL) for facilitating the injection of electrons from the cathode may be deposited on the ETL and a material for the injection layer is not particularly restricted.

LiF, NaCl, CsF, Li$_2$O, BaO, etc. may be used as the EIL material. The deposition conditions of the HBL, the ETL, and the EIL vary according to the type of compound to be used, but may be almost identical to the deposition conditions for HIL.

Finally, a metal for a cathode is vacuum evaporated or sputtered on the EIL to form a cathode. The metal for a cathode may be a metal having a low work function, alloy, electric conducting compound, and a mixture thereof. Examples of such a material include Li, Mg, Al, Al—Li, Ca, Mg—In, or Mg—Ag. Also, a transmittance type cathode composed of ITO or IZO may form a front surface of the light emitting device.

The organic EL device according to an embodiment of the present invention may include one or two intermediate layers in addition to the anode, the HIL, the HTL, the EML, the ETL, the EIL, and the cathode as illustrated in FIG. 1.

The compound represented by Formula (1) is useful as a light emitting material having superior light emitting property and hole transport property, in particular, as a host, and may also be used as a hole injection material and/or a hole transport material of blue, green, red fluorescent and phosphorescent devices.

Representative groups used in Formula (1) will now be defined.

Specific examples of the unsubstituted C1-C30 alkyl group in Formula (1) include methyl, ethyl, propyl, isobutyl, sec-butyl, pentyl, iso-amyl, hexyl, and the like. At least one hydrogen atom on the alkyl group may be substituted with a halogen atom, a C1-C30 alkyl group, a C1-C30 alkoxy group, a lower alkylamino group, a hydroxy group, a nitro group, a cyano group, an amino group, an amidino group, hydrazine, hydrazone, a carboxyl group, a sulfonic acid group, a phosphoric acid group, etc.

Specific examples of the unsubstituted C2-C30 alkenyl group in Formula (1) include an ethylene group, a propylene group, an isobutylene group, a vinyl group, and an allyl group. At least one hydrogen atom on the alkenyl group may be substituted with a halogen atom, a C1-C30 alkyl group, a C1-C30 alkoxy group, a lower alkylamino group, a hydroxy group, a nitro group, a cyano group, an amino group, an amidino group, hydrazine, hydrazone, a carboxyl group, a sulfonic acid group, a phosphoric acid group, etc.

Specific examples of the unsubstituted C1-C30 alkoxy group in Formula (1) include methoxy, ethoxy, propoxy, isobutyloxy, sec-butyloxy, pentyloxy, iso-amyloxy, and hexyloxy. At least one hydrogen atom on the alkoxy group may be substituted with the same substituent as in the above-described C1-C20 alkyl group.

The aryl group in Formula (1) is a carbocyclic aromatic system that includes one or more rings, in which the rings may be attached or fused by a pendent method. Specific examples of the aryl group include phenyl, naphthyl, tetrahydronaphthyl, and the like. At least one hydrogen atom on the aryl group may be substituted with the same substituent as in the above-described C1-C20 alkyl group.

The heteroaryl group in Formula (1) is a monovalent monocylclic ring system, which contains one, two or three heteroatoms selected from N, O, P, and S and has carbon atoms as the remaining ring atoms, in which the rings may be attached or fused by a pendent method. Examples of such a heteroaryl group include pyridyl, thienyl, furyl, and the like.

The heterocyclic group in Formula (1) is a monocylclic system, which contains one, two or three heteroatoms selected from N, O, P, and S and has carbon atoms as the remaining ring atoms, in which some hydrogen atoms on the cycloalkyl group are substituted with lower alkyl groups. At least one hydrogen atom on the cycloalkyl group may be substituted with the same substituent as in the above-described C1-C20 alkyl group.

The present invention will be described in greater detail with reference to the following examples. The following examples are for illustrative purposes and are not intended to limit the scope of the invention.

SYNTHESIS EXAMPLE

Preparation of Compound Represented by Formula 3

Compound represented by Formula 3 was synthesized according to the reaction scheme 2.

Reaction Scheme 2

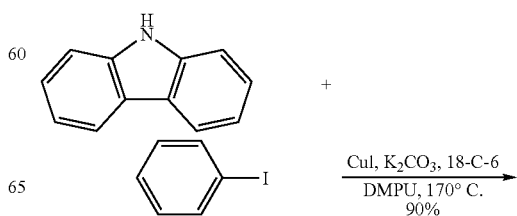

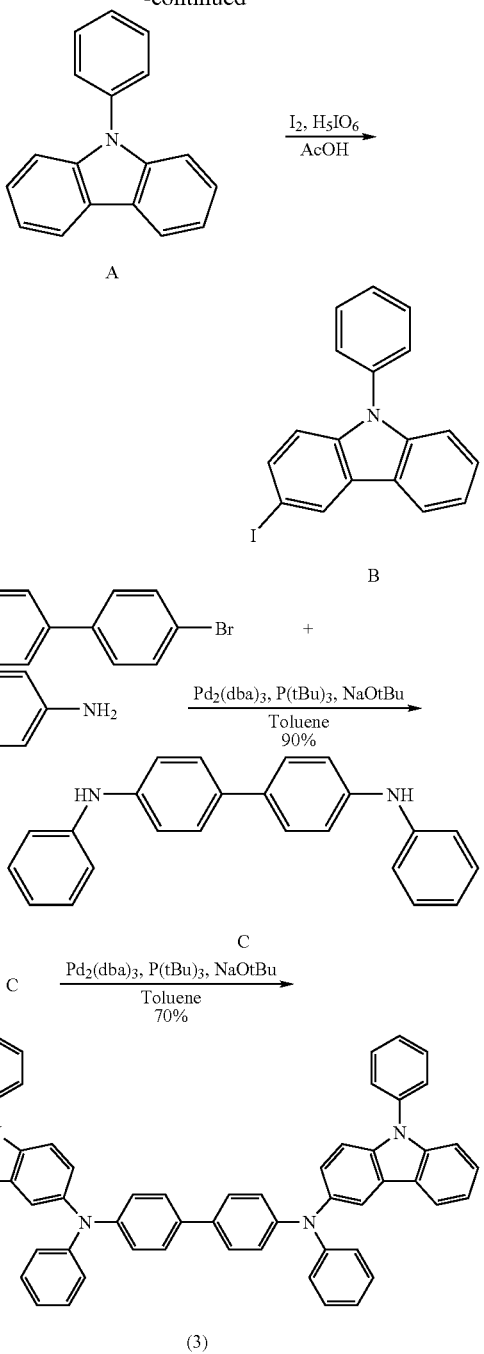

Synthesis of Intermediate Compound A

Carbazole (16.7 g, 100 mmol), iodobenzene (26.5 g, 130 mmol), CuI (1.9 g, 10 mmol), $K_2CO_3$ (138 g, 1 mol), and 18-crown-6 (530 mg, 2 mmol) were dissolved in 1,3-dimethyl-3,4,5,6-tetrahydro-(1H)-pyrimidinone (DMPU) (500 mL), and then heated at 170° C. for 8 hrs.

After the reaction was completed, the reaction mixture was cooled to room temperature and solid materials were filtered. A small amount of aqueous ammonia was added to the filtrate, and the resultant was three times washed with diethyl ether (300 mL). The washed diethyl ether layer was dried on $MgSO_4$ and dried under reduced pressure to obtain a crude product. The crude product was purified with a silica gel column chromatography to obtain 22 g of the intermediate compound A as a white solid (yield: 90%).

$^1$H NMR (CDCl$_3$, 400 MHz) δ (ppm) 8.12 (d, 2H), 7.58-7.53 (m, 4H), 7.46-7.42 (m, 1H), 7.38 (d, 4H), 7.30-7.26 (m, 2H); $^{13}$C NMR (CDCl$_3$, 100 MHz) δ (ppm) 141.0, 137.9, 130.0, 127.5, 127.3, 126.0, 123.5, 120.4, 120.0, 109.9.

Synthesis of Intermediate Compound B 2.433 g (10 mmol) of the intermediate compound A was added to 100 mL of 80% acetic acid, and then 1.357 g (5.35 mmol) of iodine (I2) and 0.333 g (1.46 mmol) of ortho-periodinic acid ($H_5IO_6$) were added thereto. The resultant was stirred under nitrogen atmosphere at 80° C. for 2 hrs.

After the reaction was completed, the reaction mixture was three times extracted with ethyl ether (50 mL). The collected organic layer was dried on magnesium sulfate and the solvent was evaporated. The residue was purified with a silica gel column chromatography to obtain 3.23 g of the intermediate compound B as a white solid (yield: 87%).

$^1$H NMR (CDCl$_3$, 300 MHz) δ (ppm) 8.43 (d, 1H), 8.05 (d, 1H), 7.62 (dd, 1H), 7.61-7.75 (m, 2H), 7.51-7.43 (m, 3H), 7.41-7.35 (m, 2H), 7.27 (dd, 1H), 7.14 (d, 1H)

Synthesis of Intermediate Compound C 3.12 g (10 mmol) of 4,4'-dibromodiphenyl, 2.3 mL (25 mmol) of aniline, 2.9 g (30 mmol) of t-BuONa, 183 mg (0.2 mmol) of $Pd_2(dba)_3$, and 20 mg (0.1 mmol) of $P(t-Bu)_3$ were dissolved in 30 mL of toluene, and then stirred at 90° C. for 3 hrs.

The reaction mixture was cooled to room temperature and three times extracted with distilled water and diethyl ether. Precipitates in an organic layer were filtered, washed with acetone and diethyl ether, and then dried in vacuum to obtain 0.3 g of the intermediate compound C (yield: 90%). The structure of the intermediate compound C was identified with $^1$H NMR.

$^1$H NMR (DMSO-d$_6$, 400 MHz) δ (ppm) 8.22 (s, 2H), 7.48 (d,4H), 7.23 (t, 4H), 7.10 (dd, 8H), 6.82 (t, 2H); $^{13}$C NMR (DMSO-d$_6$, 100 MHz) δ (ppm) 145.7, 144.3, 133.7, 131.4, 128.7, 121.2, 119.2, 118.9.

Synthesis of Compound Represented by Formula 3

912 mg (2.47 mmol) of the intermediate compound B, 336.4 mg (1 mmol) of the intermediate compound C, 300 mg (3 mmol) of t-BuONa, 40 mg (0.02 mmol) of $Pd_2(dba)_3$, and 3 mg (0.01 mmol) of $P(t-Bu)_3$ were dissolved in 5 mL of toluene, and then stirred at 90° C. for 3 hrs.

After the reaction was completed, the resultant was cooled to room temperature and three times extracted with distilled water and diethyl ether. The collected organic layer was dried on magnesium sulfate and the solvent was evaporated. The residue was purified with a silica gel column chromatography to obtain 570 mg of Compound represented by Formula 3 as a yellow solid (yield: 70%).

$^1$H NMR (CDCl$_3$, 300 MHz) δ (ppm) 7.99 (d, 2H), 7.95 (s, 2H), 7.61-7.57 (m, 8H), 7.48-7.32 (m, 12H), 7.27-7.19 (m, 8H), 7.18-7.10 (m, 8H), 6.96 (t, 2H); $^{13}$C NMR (CDCl$_3$, 100 MHz) δ (ppm) 148.4, 147.3, 141.3, 140.4, 138.0, 137.6, 133.9, 129.9, 129.1, 127.4, 127.1, 127.0, 126.1, 125.6, 124.3, 123.0, 122.9, 122.8, 121.7, 120.5, 119.9, 118.5, 110.7, 109.9.

Figure 2:
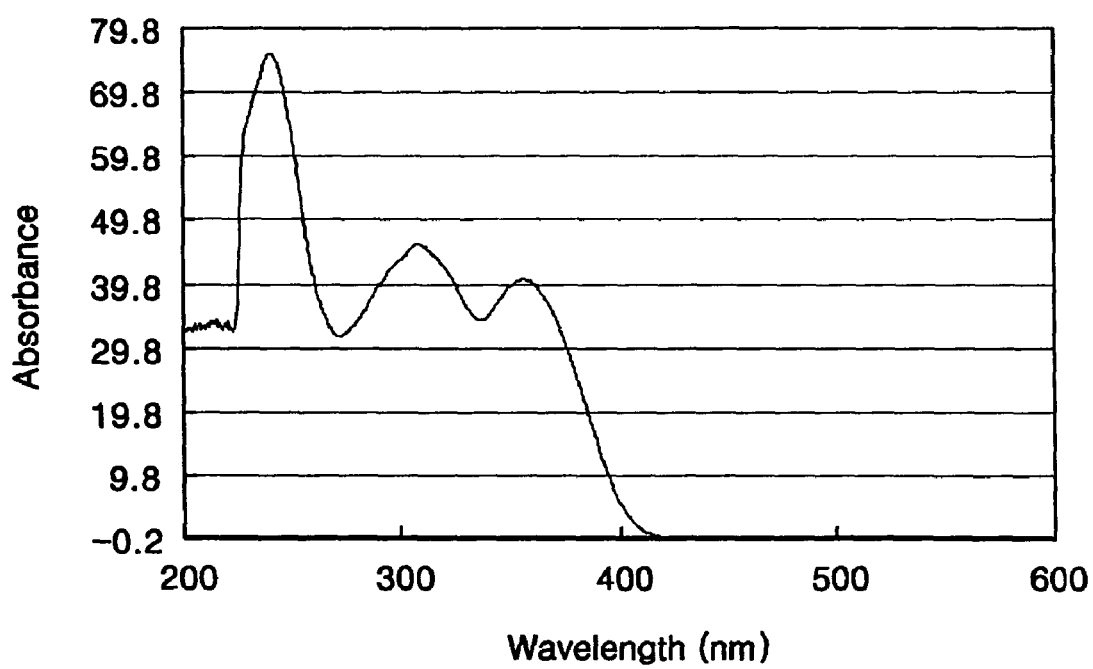
FIG. 2 illustrates a UV spectrum of Compound represented by Formula 3 obtained according to an embodiment of the present invention.

The obtained Compound represented by Formula 3 was diluted with CHCl$_3$ to a concentration of 0.2 mM and the UV spectrum therefor was obtained. A maximum absorption wavelength of 351 nm was observed in the UV spectrum (FIG. 2).

Figure 3:
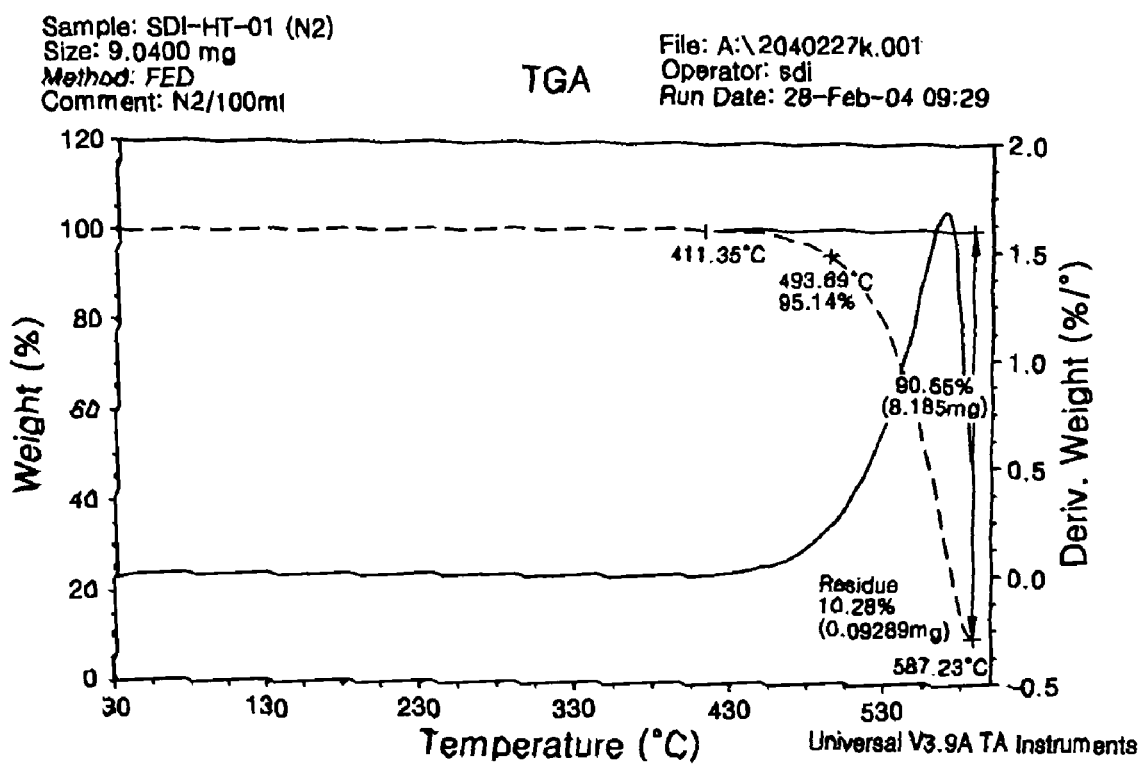
FIGS. 3 and 4 illustrate differential scanning calorimetry (DSC) and thermo gravimetric analysis (TGA) results of Compound represented by Formula 3 obtained according to an embodiment of the present invention.
Figure 4:
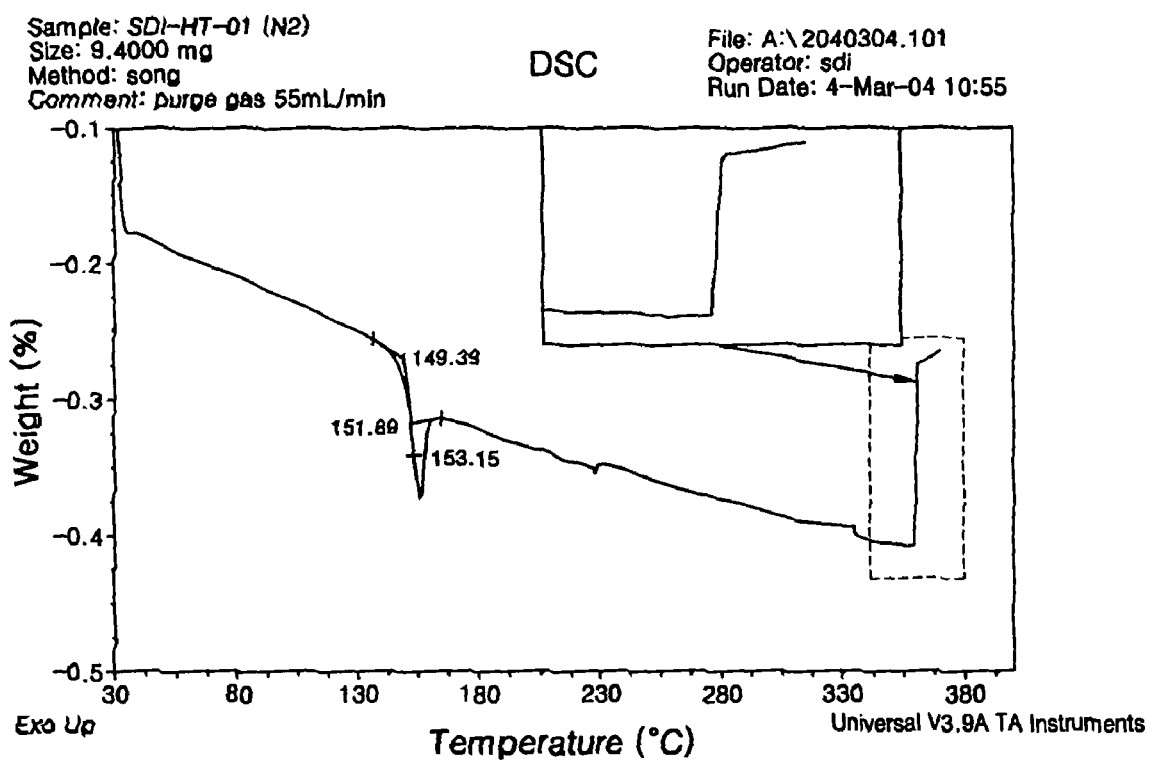

Further, Compound represented by Formula 3 was subjected to thermal analysis using TGA (Thermo Gravimetric Analysis) and DSC (Differential Scanning Calorimetry) (N₂ atmosphere, temperature range: room temperature-600° C. (10° C./min)—TGA, room temperature-400° C.—DSC, Pan type: Pt pan in disposable Al pan (TGA), disposable Al pan (DSC)) to obtain Td 494° C. and Tg 153° C. (FIGS. 3 and 4).

A HOMO (Highest Occupied Molecular Orbital) energy level of 5.16 eV and a LUMO (Lowest Occupied Molecular Orbital) energy level of 2.16 eV were obtained using UV absorption spectrum and a potentiometer AC-2.

SYNTHESIS EXAMPLE 2

Preparation of Compound Represented by Formula 4

Compound represented by Formula 4 was synthesized according to the reaction scheme 3.

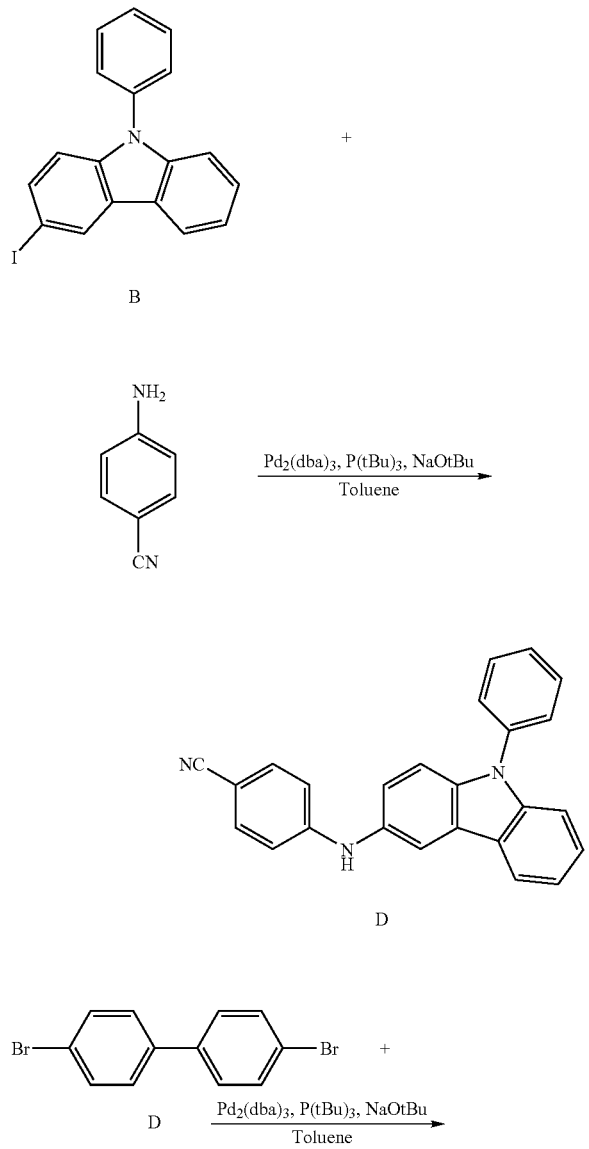

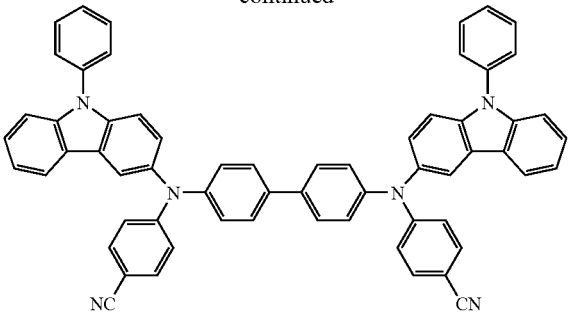

(4)

Synthesis of Intermediate Compound D 3.69 g (10 mmol) of the intermediate compound B, 1.42 g (12 mmol) of 4-aminobenzonitrile, 1.44 g (15 mmol) of t-BuONa, 183 mg (0.2 mmol) of Pd₂(dba)₃, and 40 mg (0.2 mmol) of P(t-Bu)₃ were dissolved in 50 mL of toluene, and then stirred at 90° C. for 3 hrs.

After the reaction was completed, the reaction mixture was cooled to room temperature and three times extracted with distilled water and diethyl ether. The collected organic layer was dried on magnesium sulfate and the solvent was evaporated. The residue was purified with a silica gel column chromatography to obtain 1.8 g of the intermediate compound D (yield: 50%).

Synthesis of Compound Represented by Formula 4

222 mg (0.61 mmol) of the intermediate compound D, 78 mg (0.25 mmol) of 4,4'-dibromodiphenyl, 80 mg (0.75 mmol) of t-BuONa, 310 mg (0.01 mmol) of Pd₂(dba)₃, and 2 mg (0.01 mmol) of P(t-Bu)₃ were dissolved in 5 mL of toluene, and then stirred at 90° C. for 3 hrs.

After the reaction was completed, the reaction mixture was cooled to room temperature and three times extracted with distilled water and diethyl ether. The collected organic layer was dried on magnesium sulfate and the solvent was evaporated. The residue was purified with a silica gel column chromatography to obtain 186 mg of Compound represented by Formula 4 as a yellow solid (yield: 86%).

$^1$H NMR (CDCl₃, 300 MHz) δ (ppm) 8.02 (d, 2H), 7.97 (d, 2H), 7.64-7.48 (m, 14H), 7.43-7.39 (m, 10H), 7.29-7.22 (m, 8H), 7.03 (d, 4H); $^{13}$C NMR (CDCl₃, 100 MHz) δ (ppm) 152.1, 145.6, 141.5, 138.9, 138.2, 137.3, 136.3, 133.2, 130.0, 127.9, 127.8, 127.0, 126.6, 125.8, 125.5, 124.6, 122.7, 120.5, 120.2, 119.9, 119.4, 118.9, 111.2, 110.1, 101.8.

Figure 5:
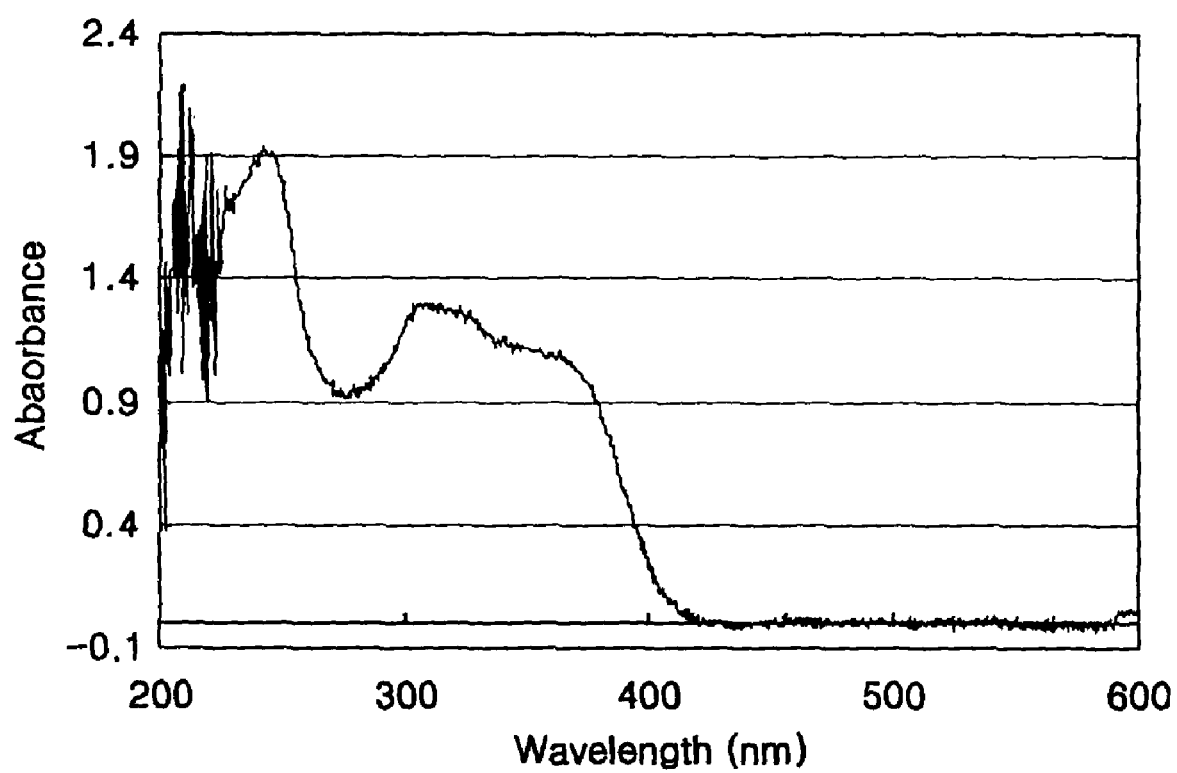
FIG. 5 illustrates a UV spectrum of Compound represented by Formula 4 obtained according to another embodiment of the present invention.

The obtained Compound represented by Formula 4 was diluted with CHCl₃ to a concentration of 0.2 mM and the UV spectrum therefor was obtained. A maximum absorption wavelength of 351 nm was observed in the UV spectrum (FIG. 5).

Figure 6:
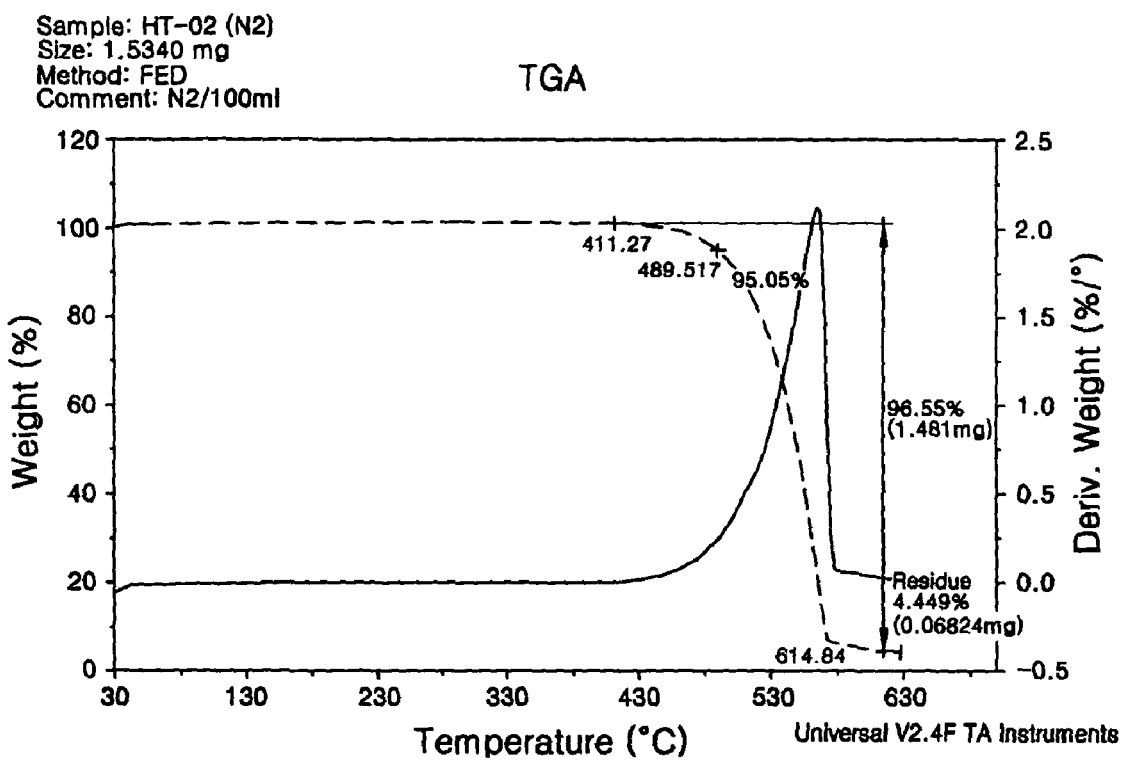
FIGS. 6 and 7 illustrate DSC and TGA analysis results of Compound represented by Formula 4 obtained according to an embodiment of the present invention.
Figure 7:
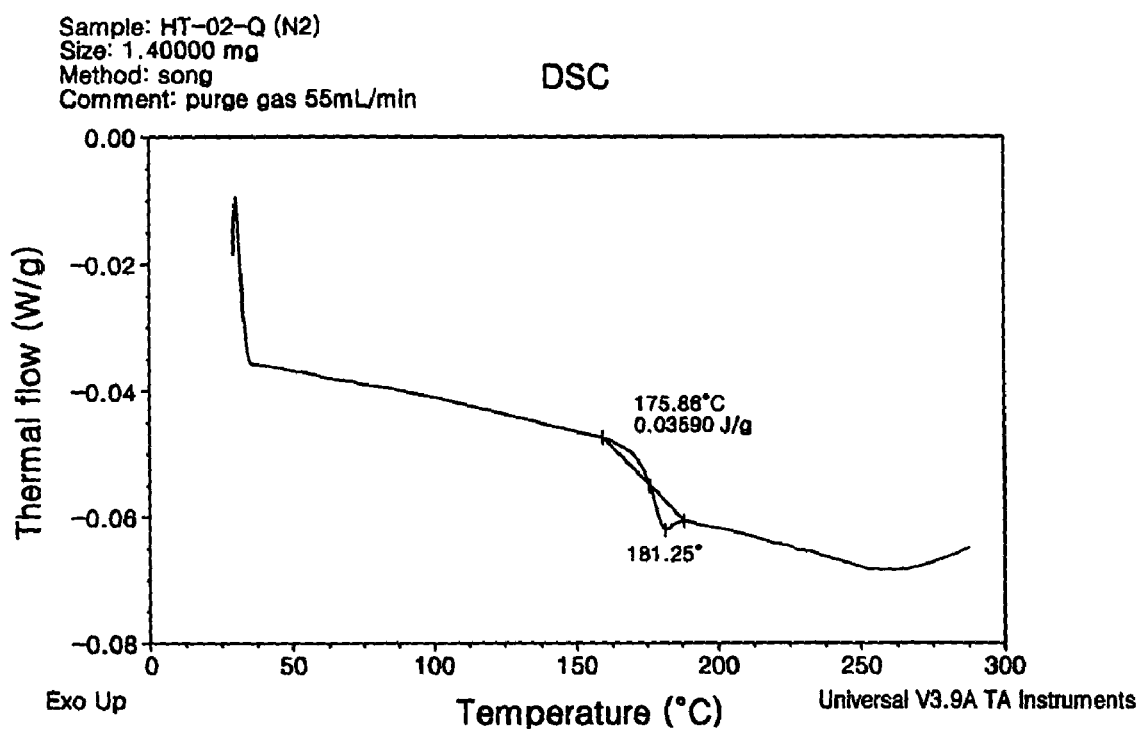

Further, Compound represented by Formula 4 was subjected to thermal analysis using TGA and DSC (N₂ atmosphere, temperature range: room temperature-600° C. (10° C./min)—TGA, room temperature-400° C.—DSC, Pan type: Pt pan in disposable Al pan (TGA), disposable Al pan (DSC)) to obtain Td 490° C., Tg 178° C., and Tm of 263° C. (FIGS. 6 and 7).

A HOMO energy level of 5.30 eV and a LUMO energy level of 2.37 eV were obtained using UV absorption spectrum and a potentiometer AC-2.

Example 1

A corning 15 Ω/cm² (1200 Å) ITO glass substrate as an anode was cut to a size of 50 mm×50 mm×0.7 mm and ultrasonically washed with isopropyl alcohol and pure water, for 5 min each wash. Then, the washed glass substrate was irradiated with a UV radiation for 30 min and washed by exposing to ozone, and then, installed in a vacuum evaporator.

Compound represented by Formula 3 was vacuum evaporated on the substrate to form a 600 Å thick HIL. Then, 4,4-bis[N-(1-naphthyl)-N-phenylamino]biphenyl (NPB) was vacuum evaporated on the HIL to form a 300 Å thick HTL.

IDE140 (available from Idemitsu Kosan Co., Ltd.), which was known as a blue fluorescent host, and IDE105 (available from Idemitsu Kosan Co., Ltd.), which was known as a blue fluorescent dopant, were co-deposited (weight ratio 98:2) on the HTL to form a 200 Å thick EML.

Alq₃ was deposited on the EML to form a 300 Å thick ETL, and then LiF was deposited on the ETL to form a 10 Å thick EIL and Al was deposited thereon to form a 3000 Å thick anode, thereby completing an organic electroluminescent device.

This device has a driving voltage of 7.1 V, a luminance of 3,214 cd/m², a color coordination (0.14, 0.15), and luminous efficiency of 6.43 cd/A at a current density of 50 mA/cm².

Comparative Example 1

An organic EL device was manufactured in the same manner as in Example 1, except that IDE 406 (available from Idemitsu Kosan Co., Ltd.) instead of Compound represented by Formula 3 was used to form a HIL.

This device has a driving voltage of 8.0 V, a luminance of 3,024 cd/m², a color coordination (0.14, 0.15), and luminous efficiency of 6.05 cd/A at a current density of 50 mA/cm².

The driving voltage of the organic EL device which used Compound represented by Formula 3 according to an embodiment of the present invention as a HIL material was approximately 1 V lower than the driving voltage of the organic EL device of Comparative Example 1 at the same current density due to an improved charge injection ability. Further, the organic EL device of Example 1 had higher current efficiency and luminance than the organic EL device of Comparative Example 1.

Figure 8:
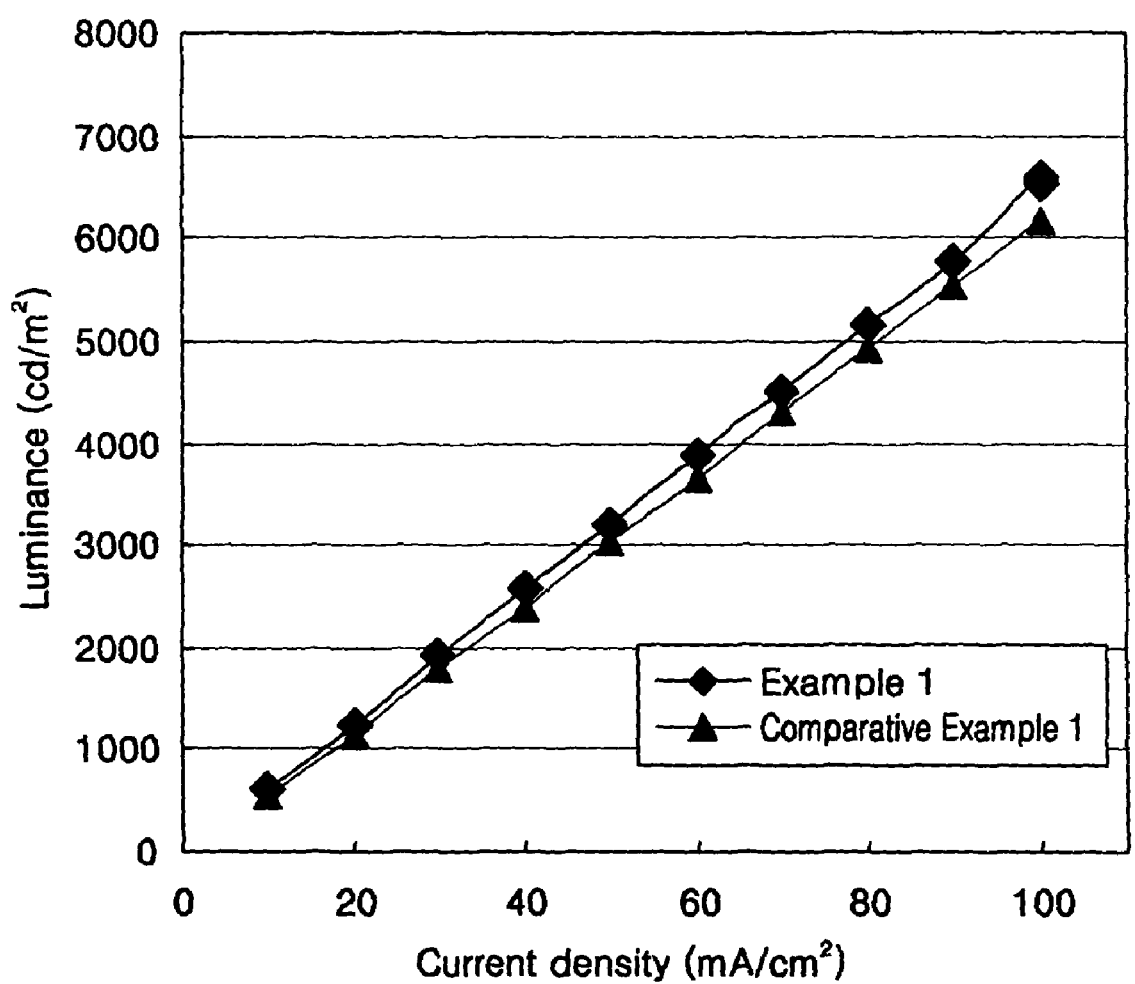
FIG. 8 is a graph illustrating the variation in luminance with respect to the current density in organic EL devices obtained in Example 1 of the present invention and Comparative Example 1.
Figure 9:
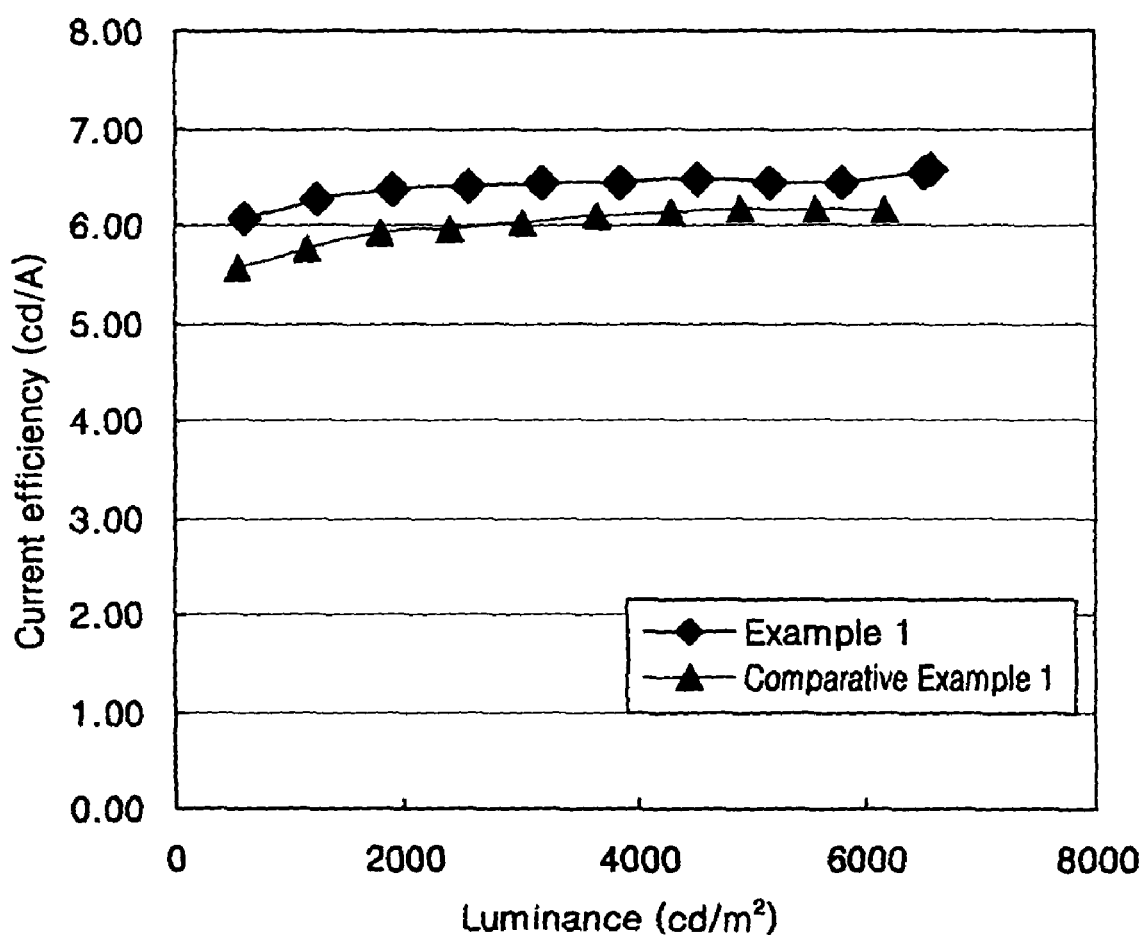
FIG. 9 is a graph illustrating the variation in current efficiency with respect to the luminance in organic EL devices obtained in Example 1 of the present invention and Comparative Example 1.

The luminance and current efficiency at the same current density for the organic EL devices are illustrated in FIGS. 8 and 9.

Example 2

A corning 15 Ω/cm² (1200 Å) ITO glass substrate as an anode was cut to a size of 50 mm×50 mm×0.7 mm and ultrasonically washed with isopropyl alcohol and pure water, for 5 min each wash. Then, the washed glass substrate was irradiated with a UV radiation for 30 min and washed by exposing to ozone, and then, installed in a vacuum evaporator.

Compound represented by Formula 3 was vacuum evaporated on the substrate to form a 600 Å thick HIL. Then, 4,4'-bis[N-(1-naphthyl)-N-phenylamino]biphenyl (NPB) was vacuum evaporated on the HIL to form a 300 Å thick HTL. Alq3, which was a green fluorescent host and C545T, which was a green fluorescent dopant, were co-deposited (weight ratio 98:2) on the HTL to form a 250 Å thick EML.

Alq₃ was deposited on the EML to form a 300 Å thick ETL, and then LiF was deposited on the ETL to form a 10 Å thick EIL and Al was deposited thereon to form a 3000 Å thick anode, thereby completing an organic EL device.

This device has a driving voltage of 6.12 V, a luminance of 8,834 cd/m², a color coordination (0.31, 0.63), and luminous efficiency of 17.67 cd/A at a current density of 50 mA/cm².

Comparative Example 2

An organic EL device was prepared in the same manner as in Example 2, except for using IDE406 (available from Idemitsu Kosan Co., Ltd.) instead of Compound represented by Formula 3 in forming a hole injection layer.

This device has a driving voltage of 6.73 V, a luminance of 7,083 cd/m², a color coordination (0.31, 0.63), and luminous efficiency of 14.17 cd/A at a current density of 50 mA/cm².

Figure 10:
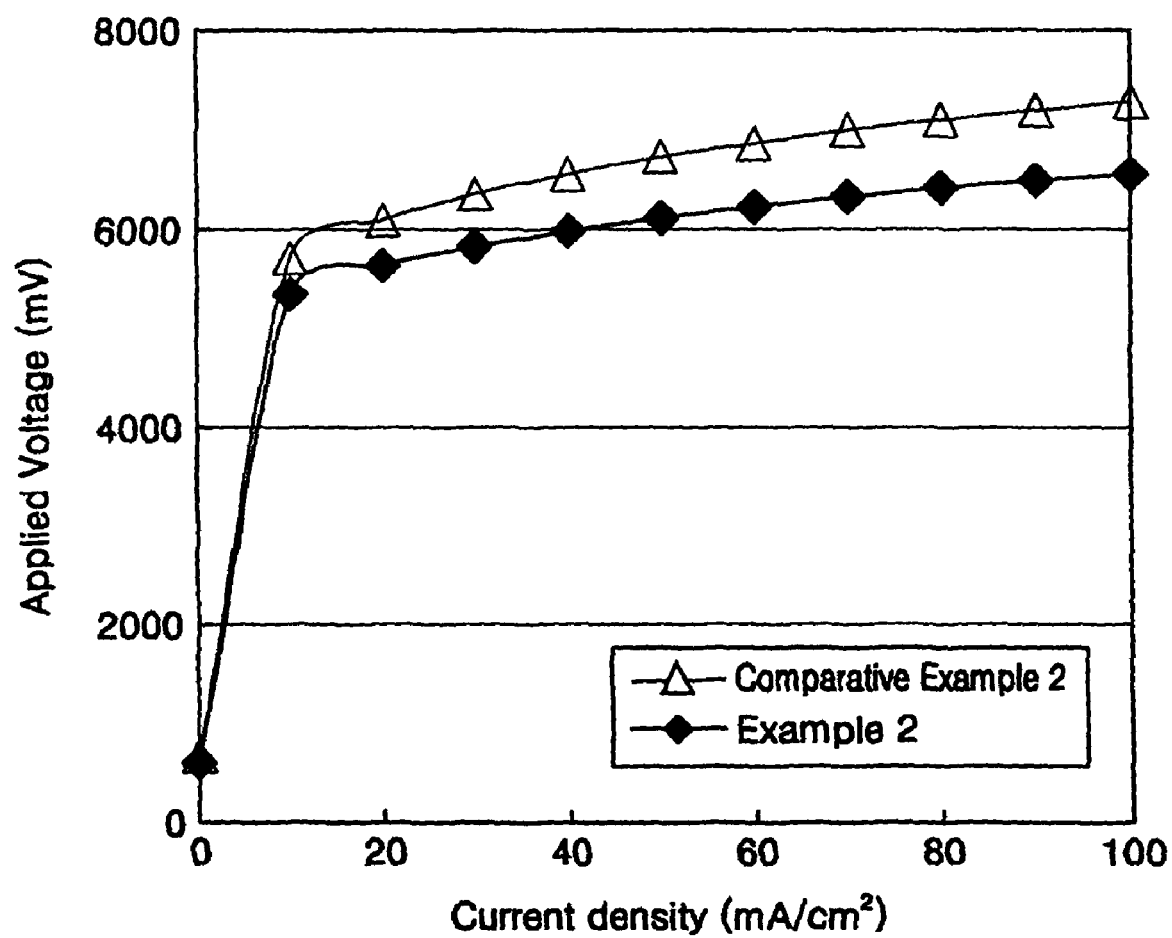
FIG. 10 is a graph illustrating the driving voltage at the same current density for the organic EL devices according to the Example 2 and Comparative Example 2.
Figure 11:
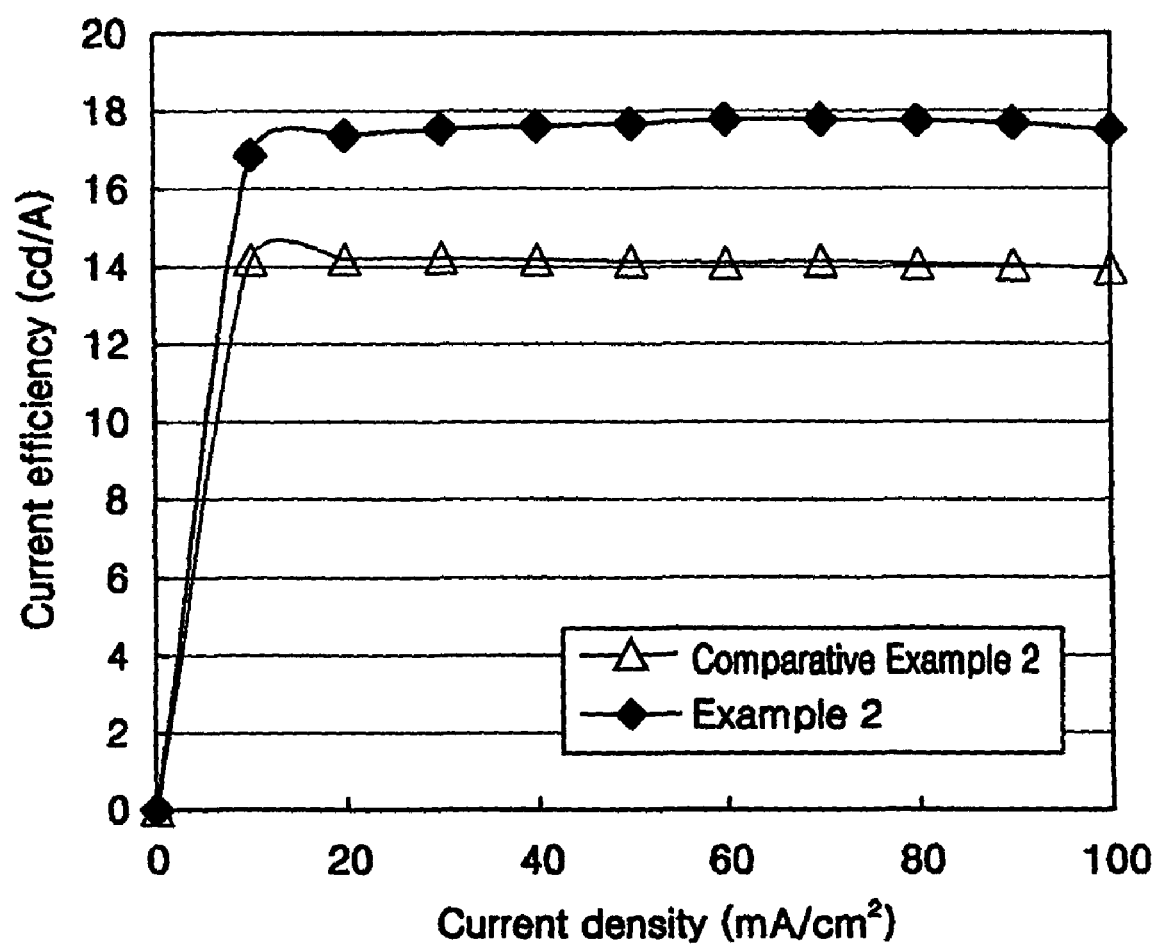
FIG. 11 is a graph illustrating the current efficiency at the same current density for the organic EL devices according to the Example 2 and Comparative Example 2.

The driving voltage and current efficiency at the same current density for the organic EL devices according to the Example 2 and Comparative Example 2 are illustrated in FIGS. 10 and 11.

As such, when the phenylcarbazole-based compound according to an embodiment of the present invention is used for material for forming hole injection layer, the capability for electron injection is enhanced, and thus a driving voltage decrease of 0.5V or more at the same current density.

As described above, the phenylcarbazole-based compound according to an embodiment of the present invention has superior electric properties and charge transport abilities, and thus is useful as a hole injection material, a hole transport material, and/or an emitting material which is suitable for fluorescent and phosphorescent devices of all colors, including red, green, blue, and white colors. The organic EL device manufactured using the phenylcarbazole-based compound has high efficiency, low voltage, high luminance, and a long lifespan.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A compound represented by Formula (1):

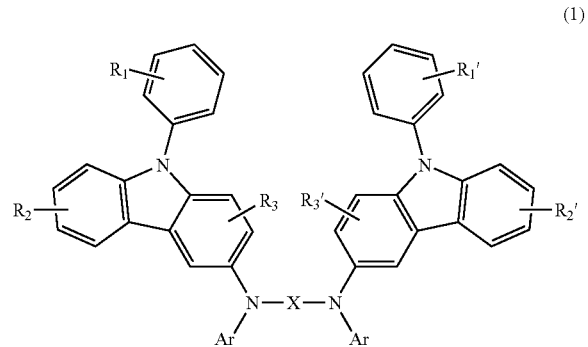

where X is selected from the group consisting of a substituted or unsubstituted C1-C30 alkylene group, a substituted or unsubstituted C2-C30 alkenylene group, a substituted or unsubstituted C6-C30 arylene group, a substituted or unsubstituted C2-C30 heteroarylene group, and a substituted or unsubstituted C2-C30 heterocycle;

each of $R_1$, $R_2$, $R_3$, $R_1'$, $R_2'$ and $R_3'$ is independently a mono or multi substituent selected from the group consisting of a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C2-C30 heterocycle, a substituted or unsubstituted C6-C30 condensed polycyclic group, a hydroxy group, a cyano group, and a substituted or unsubstituted amino group, and two or more adjacent groups among $R_1$, $R_2$, $R_3$, $R_1'$, $R_2'$ and $R_3'$ can be connected to each other to form a saturated or unsaturated carbocycle; and each Ar is independently selected from the group consisting of a phenyl group, an ethylphenyl group, an ethylbiphenyl group, an o-, m-, or p-fluorophenyl group, a dichlorophenyl group, a dicyanophenyl group, a trifluoromethoxyphenyl group, an o-, m-, or p-tolyl group, an o-, m-, and p-cumenyl group, a mesityl group, a phenoxyphenyl group, a (α,α-dimethylbenzene) phenyl group, a (N,N'-dimethyl)aminophenyl group, a (N,N'-diphenyl) aminophenyl group, a pentarenyl group, an indenyl group, a naphthyl group, a methylnaphthyl group, an anthracenyl group, an azurenyl group, a heptarenyl group, an acenaphthylrenyl group, a phenanthrenyl group, a fluorenyl group, an anthraquinolyl group, a triphenylene group, a pyrenyl group, a pherylenyl group, a chloropherylenyl group, a pentaphenyl group, a pentacenyl group, a tetraphenylenyl group, a hexaphenyl group, a coroneryl group, a trinaphthylenyl group, a heptaphenyl group, and a carbazolyl group.

2. A compound represented by one selected from the group consisting of formulae (3) through (26):

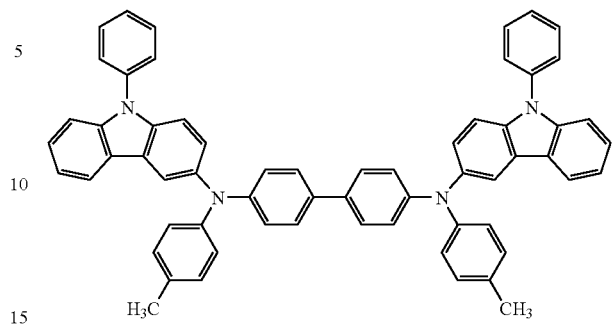

5

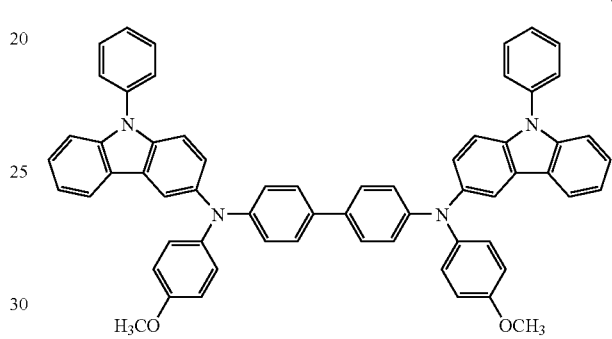

6

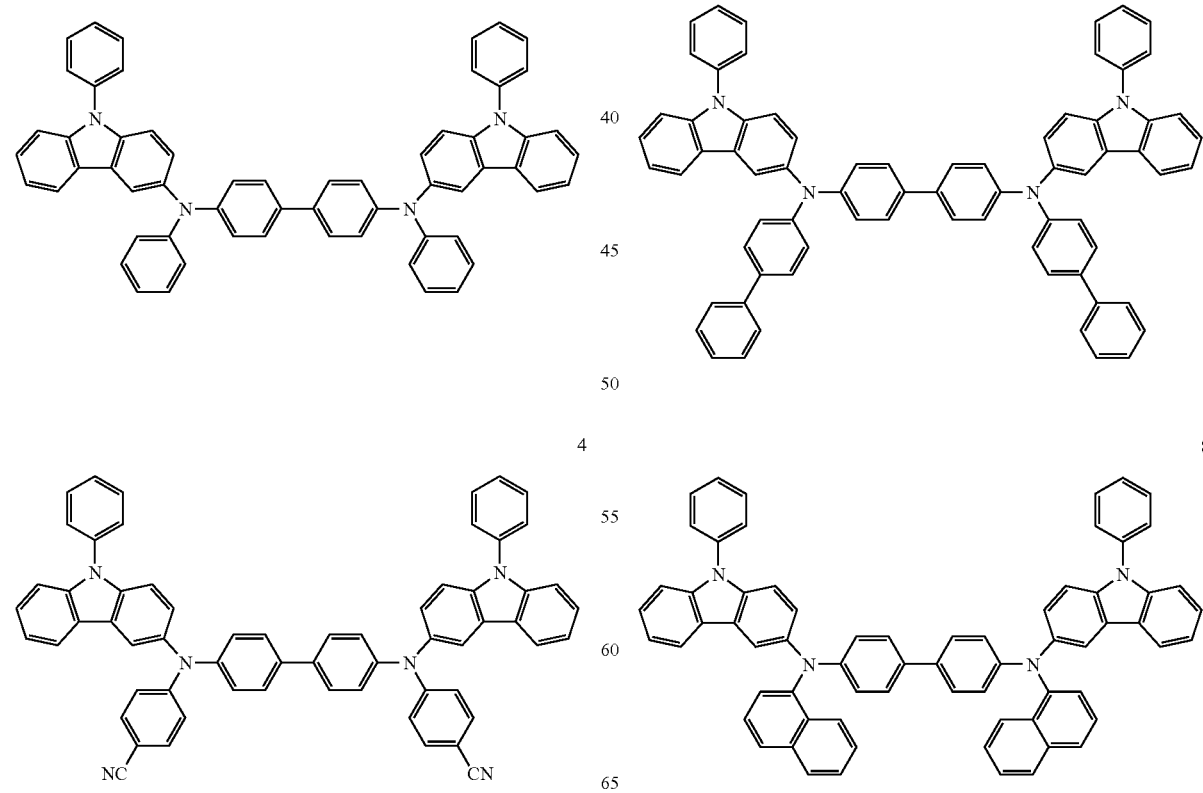

9
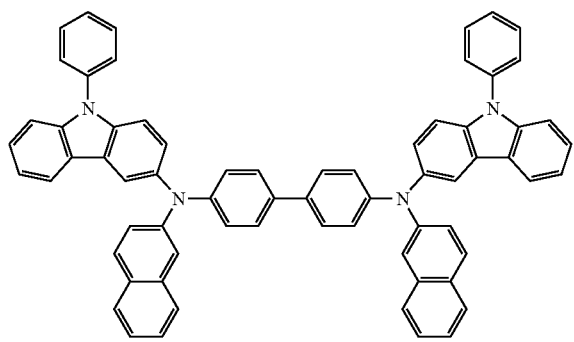
10
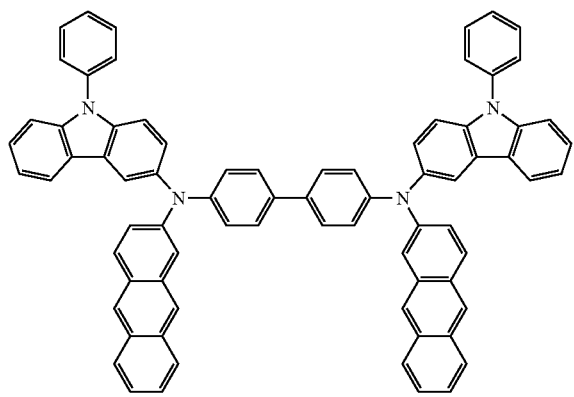
11
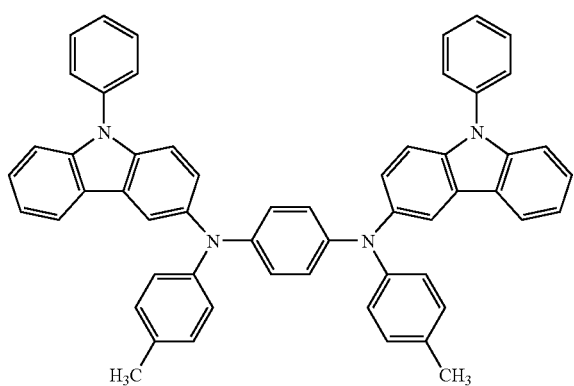
13
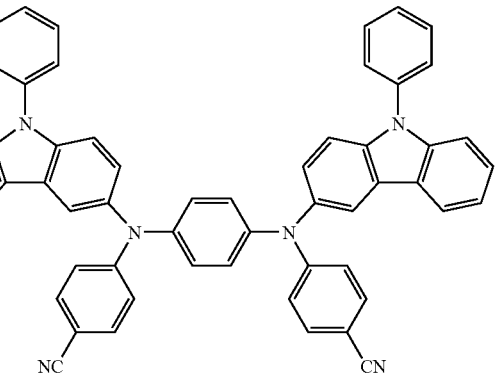
14
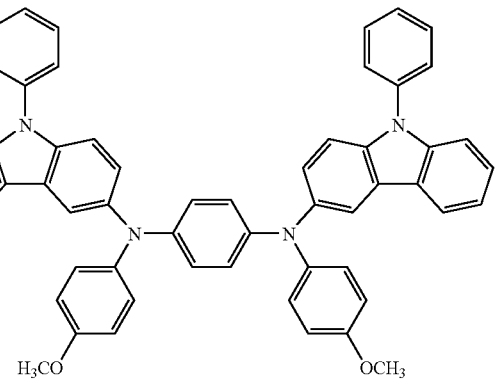
15
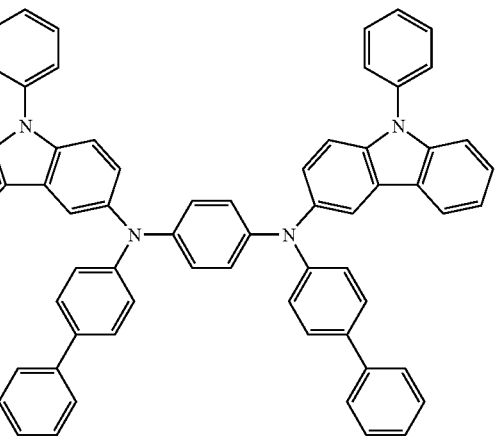
16
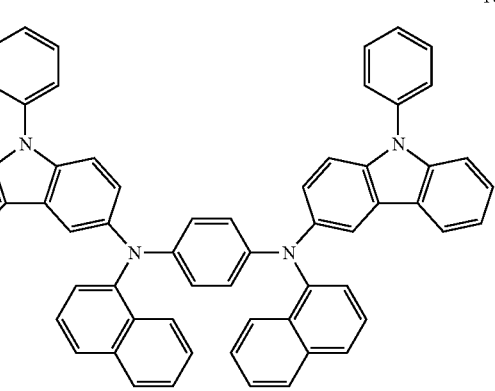

17
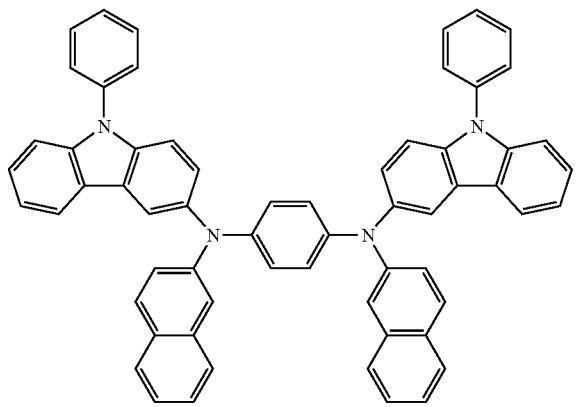
18
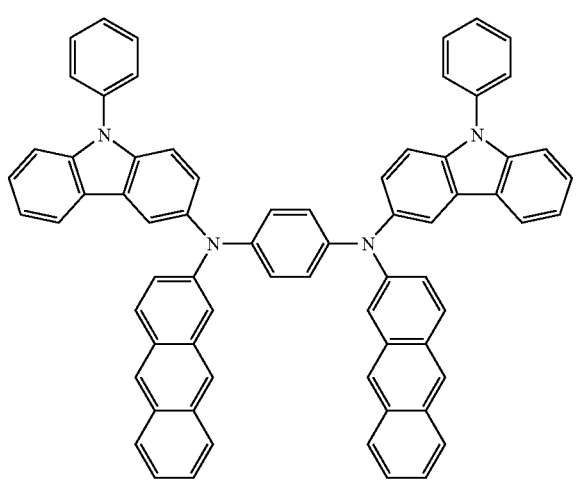
19
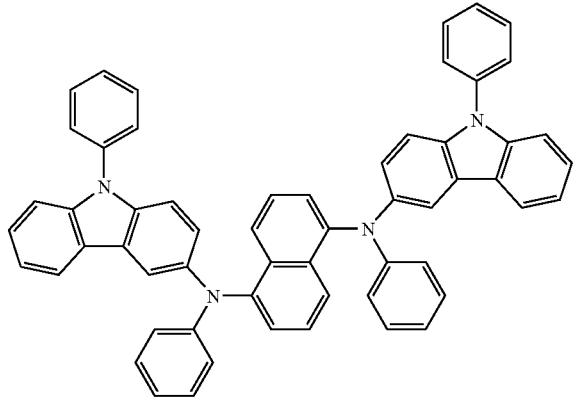
20
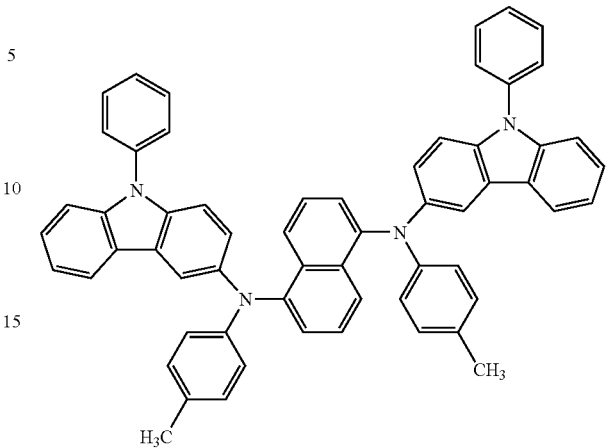
21
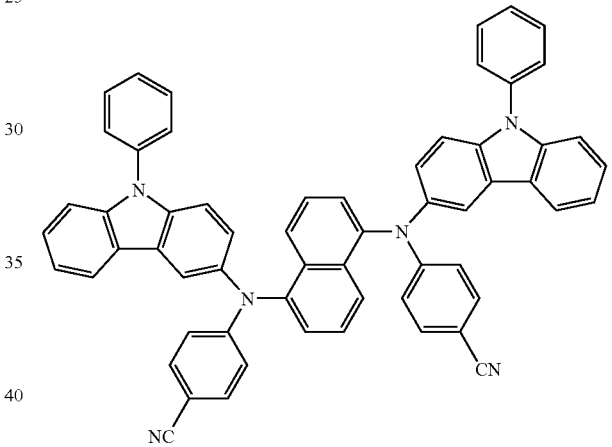
22
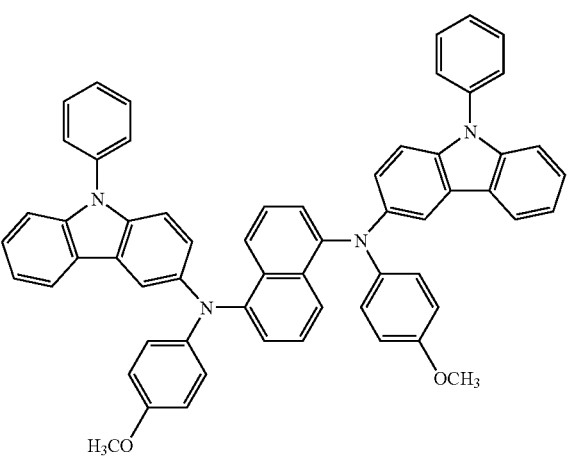

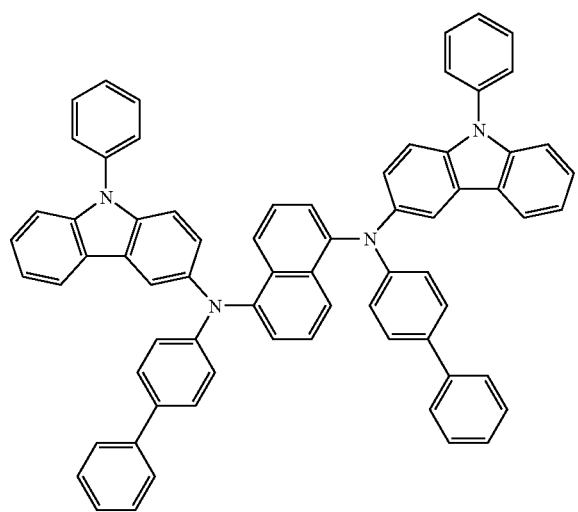

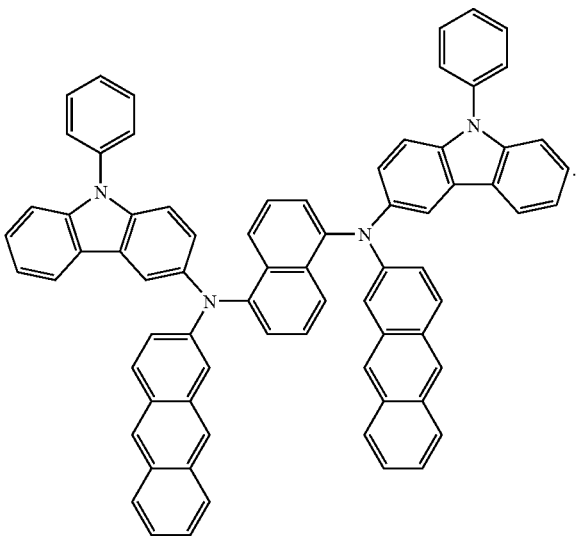

3. The compound of claim 2, wherein the compound is represented by formulae (3):

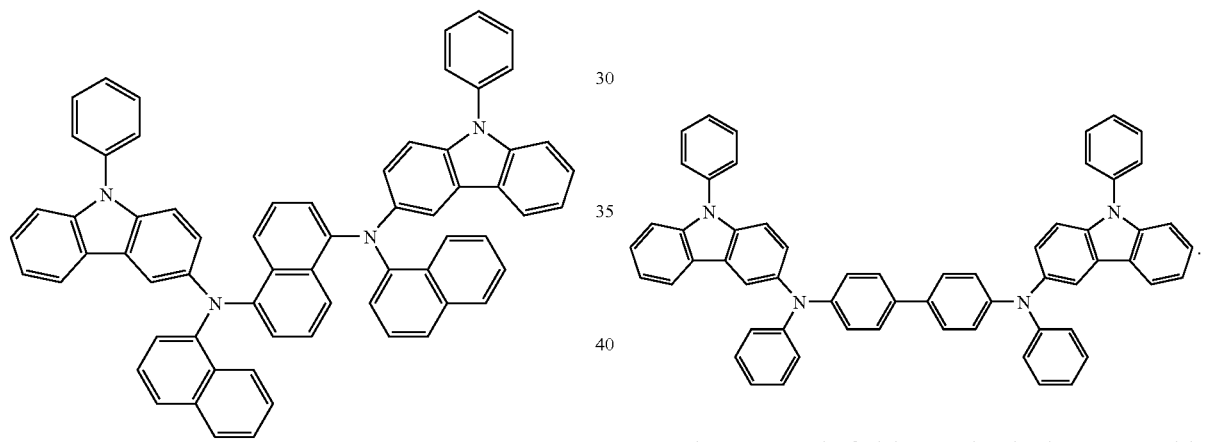

4. The compound of claim 2, wherein the compound is represented by formulae (4):

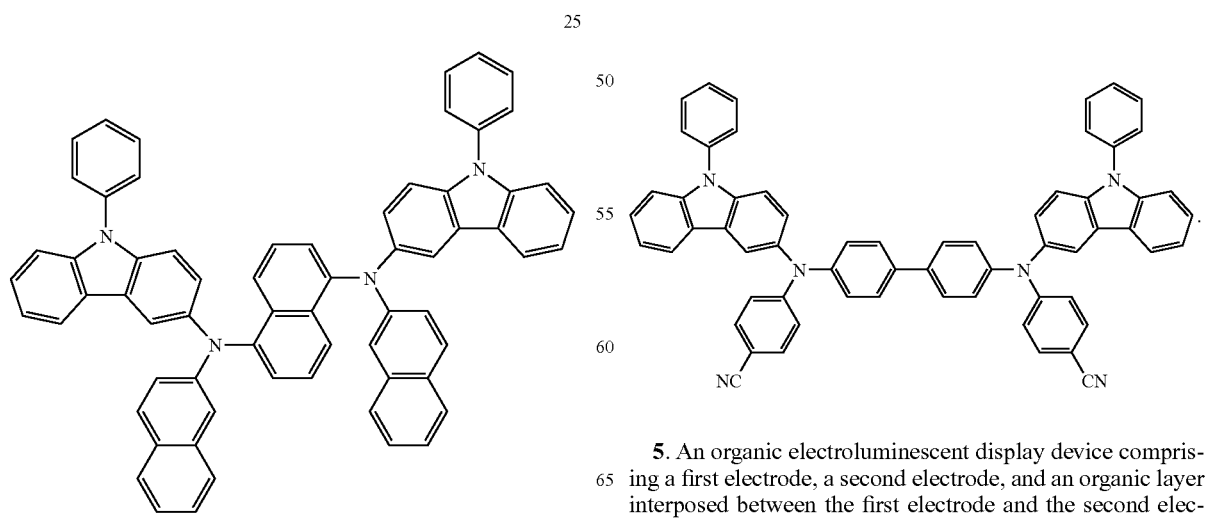

5. An organic electroluminescent display device comprising a first electrode, a second electrode, and an organic layer interposed between the first electrode and the second electrode, the organic layer comprising the compound of claim 1.

6. A method of preparing a compound represented by Formula (1), comprising:

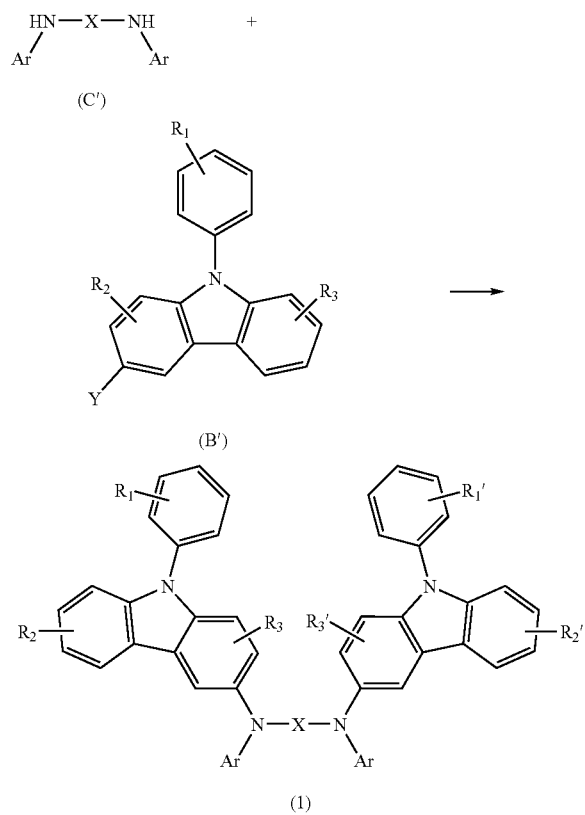

where X is selected from the group consisting of a substituted or unsubstituted C1-C30 alkylene group, a substituted or unsubstituted C2-C30 alkenylene group, a substituted or unsubstituted C6-C30 arylene group, a substituted or unsubstituted C2-C30 heteroarylene group, and a substituted or unsubstituted C2-C30 heterocycle;

each of $R_1$, $R_2$, $R_3$, $R_1'$, $R_2'$ and $R_3'$ is independently a mono or multi substituent selected from the group consisting of a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C2-C30 heterocycle, a substituted or unsubstituted C6-C30 condensed polycyclic group, a hydroxy group, a cyano group, and a substituted or unsubstituted amino group, and two or more adjacent groups among $R_1$, $R_2$, $R_3$, $R_1'$, $R_2'$ and $R_3'$ can be connected to each other to form a saturated or unsaturated carbocycle;

each Ar is a substituted or unsubstituted C6-C30 aryl group or a substituted or unsubstituted C2-C30 heteroaryl group; and Y is a halogen atom.

7. The method of claim 6, wherein the reaction is carried out in the presence of $Pd_2(dba)_3$ where dba is dibenzylideneacetone, sodium tert-butoxide, and tri(tert-butyl) phosphine at a temperature of 50 to 150° C.

8. An organic electroluminescent display device, comprising:

a first electrode;

a second electrode; and an organic layer interposed between the first electrode and the second electrode, the organic layer comprising a compound represented by formula 1:

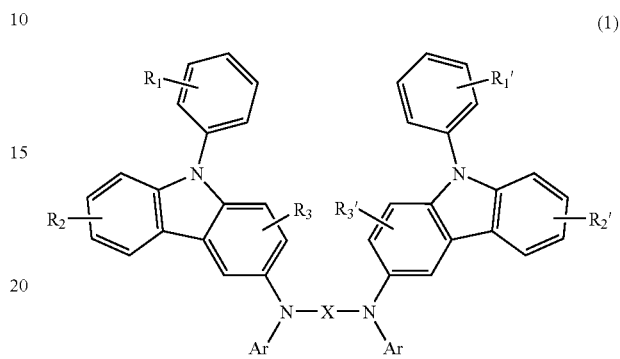

where X is selected from the group consisting of a substituted or unsubstituted C1-C30 alkylene group, a substituted or unsubstituted C2-C30 alkenylene group, a substituted or unsubstituted C6-C30 arylene group, a substituted or unsubstituted C2-C30 heteroarylene group, and a substituted or unsubstituted C2-C30 heterocycle;

each of $R_1$, $R_2$, $R_3$, $R_1'$, $R_2'$ and $R_3'$ is independently a mono or multi substituent selected from the group consisting of a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C2-C30 heterocycle, a substituted or unsubstituted C6-C30 condensed polycyclic group, a hydroxy group, a cyano group, and a substituted or unsubstituted amino group, and two or more adjacent groups among $R_1$, $R_2$, $R_3$, $R_1'$, $R_2'$ and $R_3'$ can be connected to each other to form a saturated or unsaturated carbocycle; and each Ar is a substituted or unsubstituted C6-C30 aryl group or a substituted or unsubstituted C2-C30 heteroaryl group, wherein the substituent of the substituted C6-C30 aryl group and the substituted C2-C30 heteroaryl group are each independently selected from the group consisting of a C1-C10 alkyl group, a C1-C10 alkoxy group, a nitro group, a halogen atom, an amino group, a C6-C10 aryl group, a C2-C10 heteroaryl group, a cyano group, and a hydroxy group.

9. The organic electroluminescent device of claim 8, wherein the organic layer is a hole injection layer or a hole transport layer.

10. The organic electroluminescent device of claim 8, wherein the organic layer is a single layer serving as both a hole injection layer and a hole transport layer.

11. The organic electroluminescent device of claim 8, wherein the organic layer is an emitting layer.

12. The organic electroluminescent device of claim 11, wherein the emitting layer is composed of a phosphorescent or fluorescent material.

13. The organic electroluminescent device of claim 11, wherein the compound represented by Formula (1) is used as a fluorescent or phosphorescent host in the emitting layer.

14. An organic electroluminescent device, comprising:
a first electrode;
a second electrode; and
an organic layer interposed between the first electrode and the second electrode, the organic layer comprising a compound represented by one selected from the group consisting of the following formulae:
3
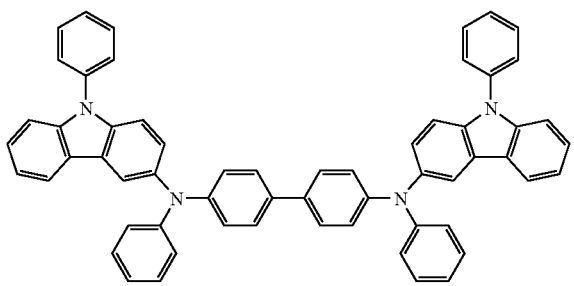
4
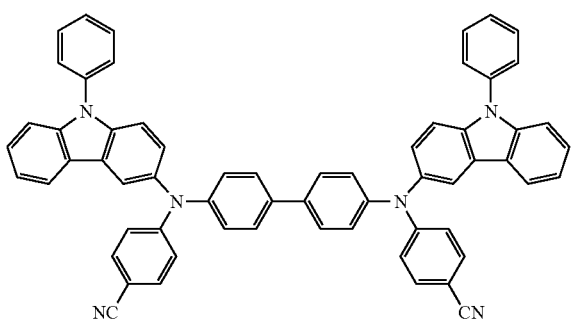
5
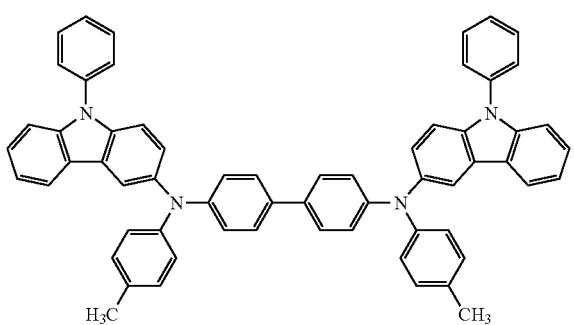
6
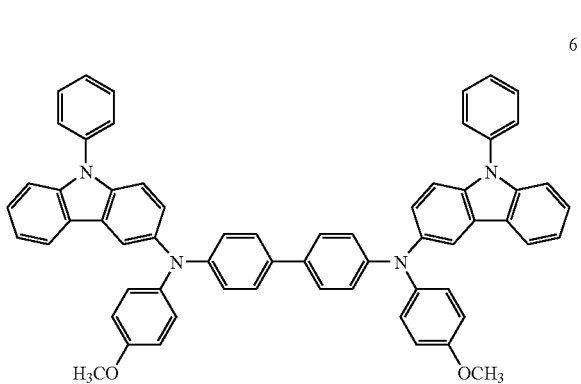
-continued
7
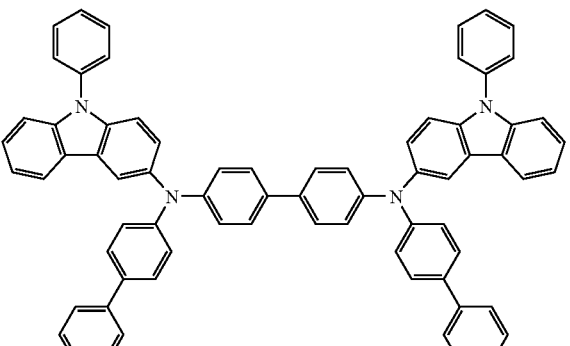
8
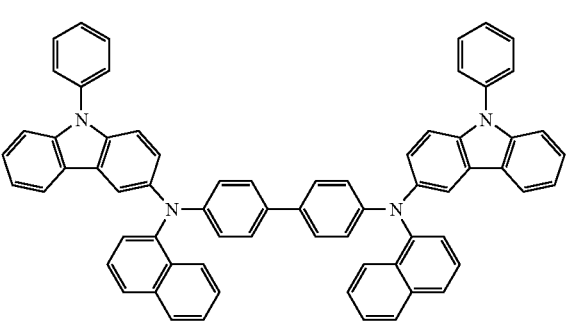
9
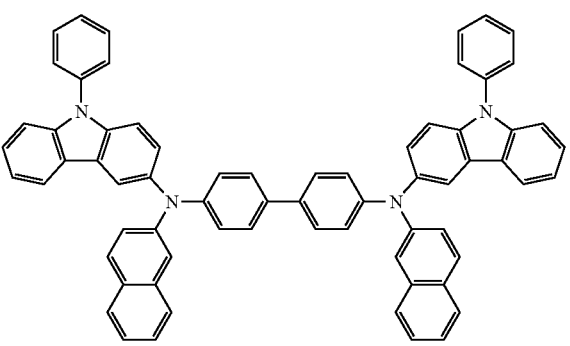
10
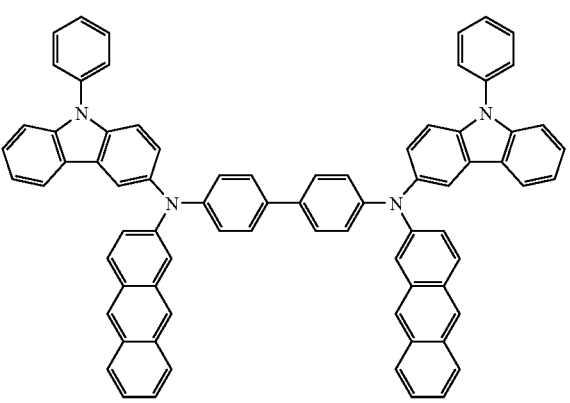

35
-continued
11
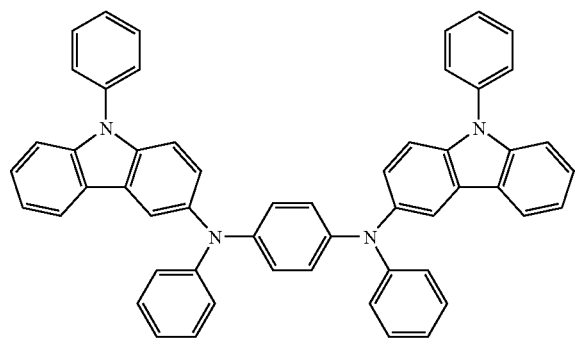
12
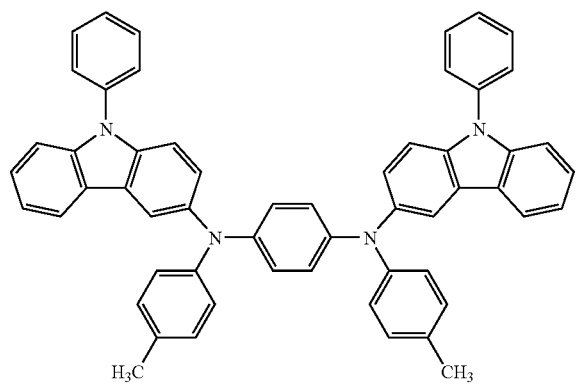
13
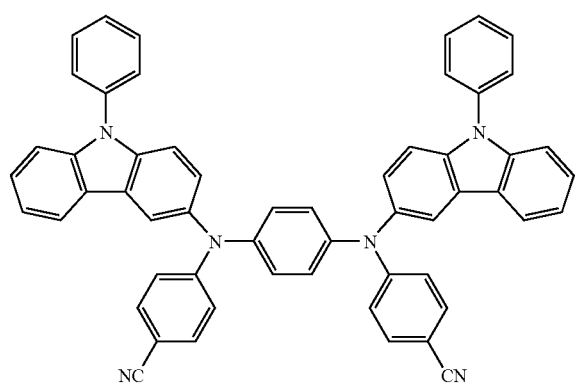
14
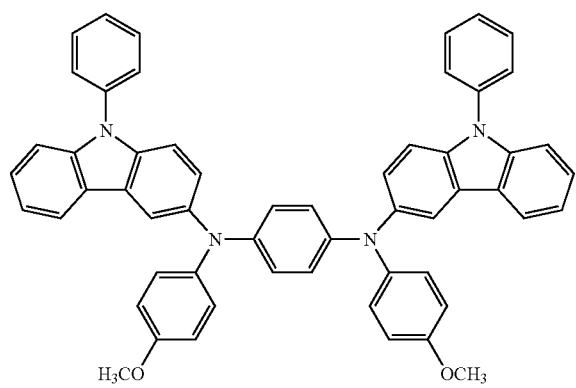
36
-continued
15
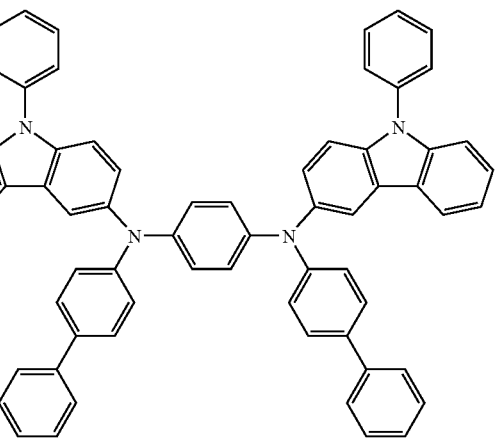
16
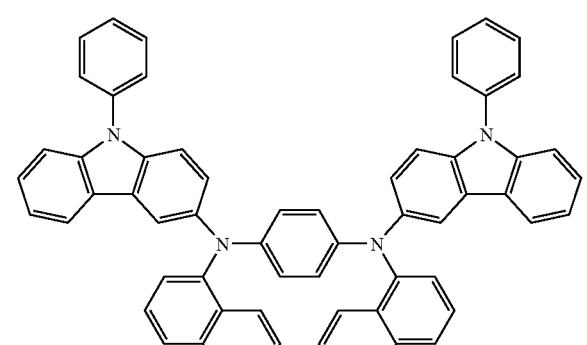
17
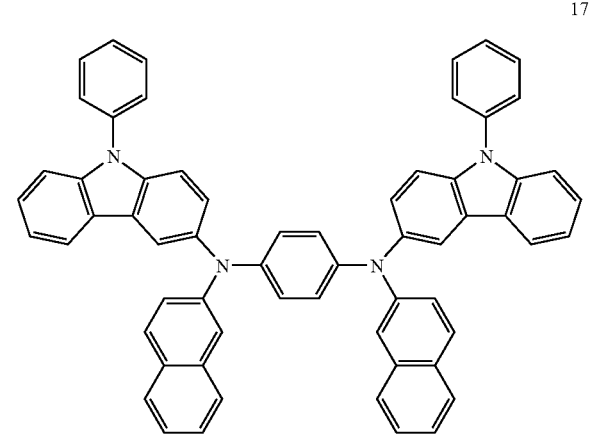

18
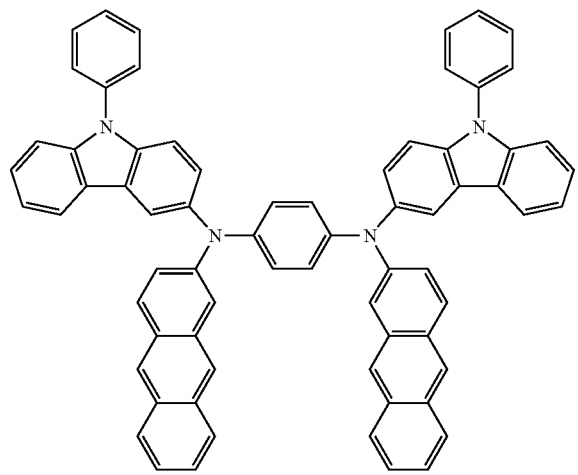
19
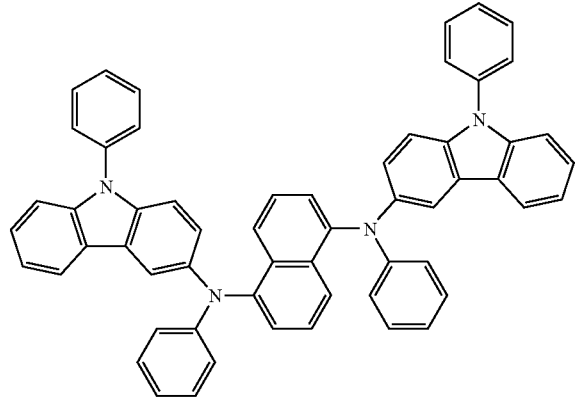
20
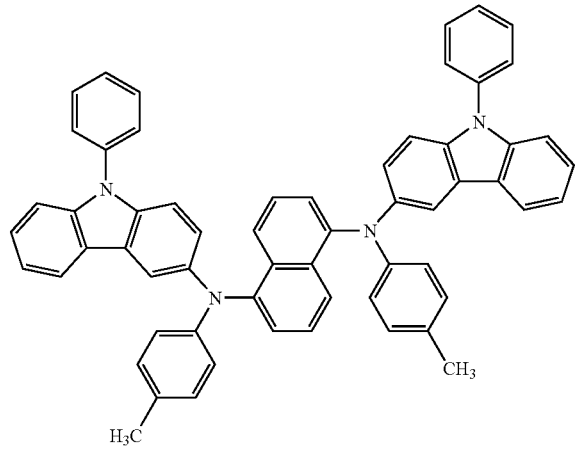
21
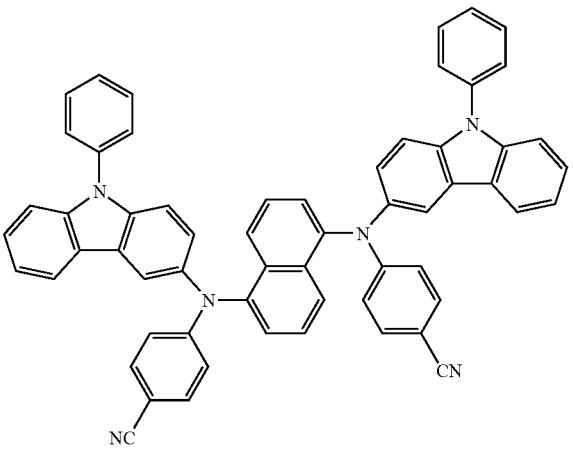
22
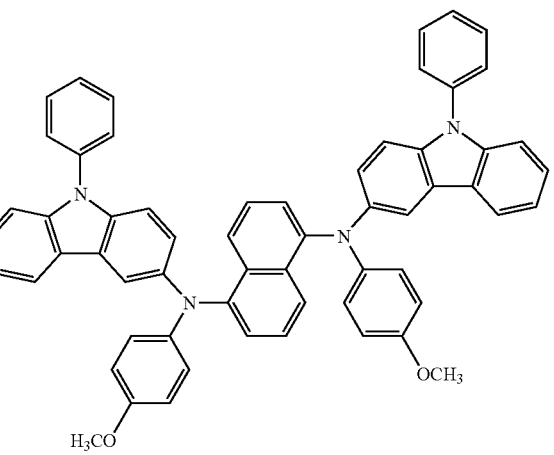
23
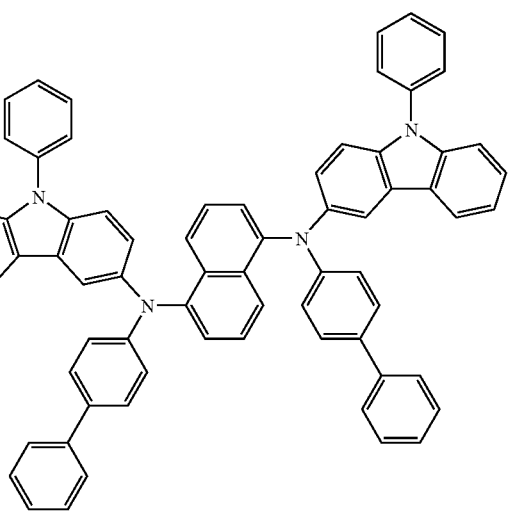

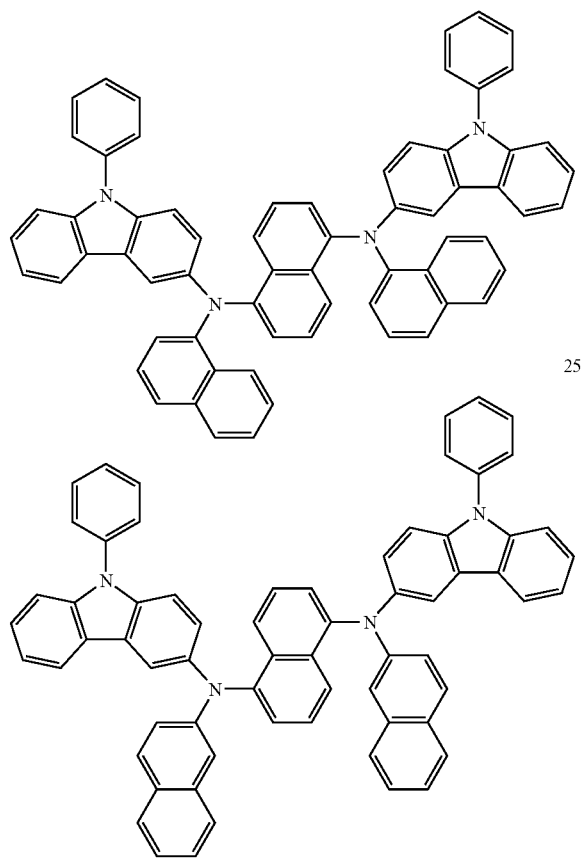
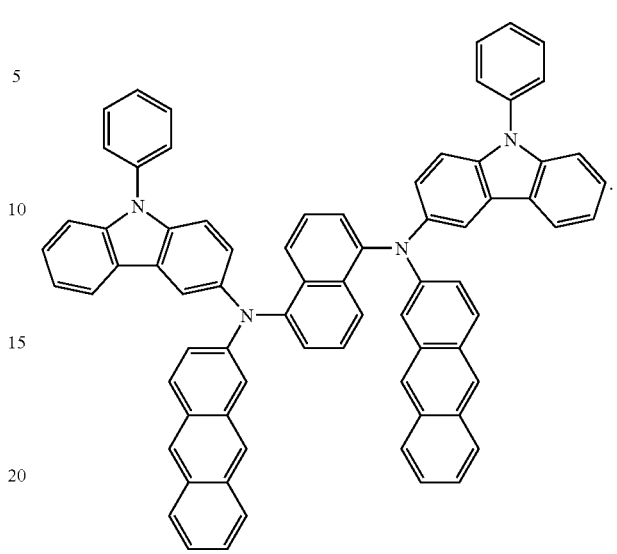
15. The organic electroluminescent device of claim 14, wherein the compound is represented by Formula (3) or Formula (4):
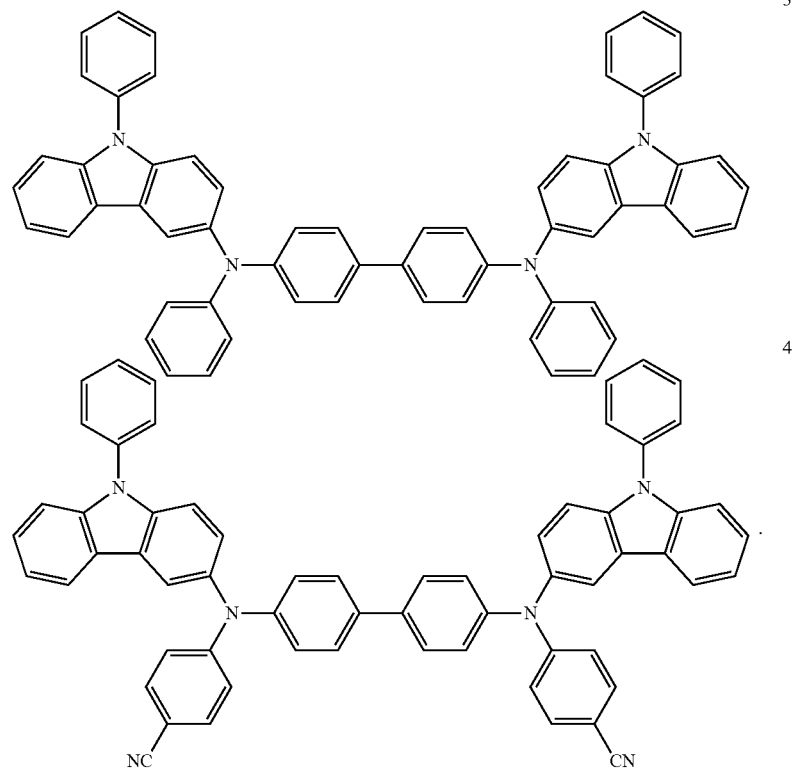
* * * * *